US009872968B2

(12) United States Patent
de Zambotti et al.

(10) Patent No.: US 9,872,968 B2
(45) Date of Patent: Jan. 23, 2018

(54) BIOFEEDBACK VIRTUAL REALITY SLEEP ASSISTANT

(71) Applicant: SRI International, Menlo Park, CA (US)

(72) Inventors: Massimiliano de Zambotti, Burlingame, CA (US); Ian M. Colrain, Redwood City, CA (US); Fiona C. Baker, San Jose, CA (US); Rakesh Kumar, West Windsor, NJ (US); Mikhail Sizintsev, Plainsboro, NJ (US); Supun Samarasekera, Princeton, NJ (US); Glenn A. Murray, Jamison, PA (US)

(73) Assignee: SRI INTERNATIONAL, Menlo Park, CA (US)

( * ) Notice: Subject to any disclaimer, the term of this patent is extended or adjusted under 35 U.S.C. 154(b) by 826 days.

(21) Appl. No.: 14/251,024

(22) Filed: Apr. 11, 2014

(65) Prior Publication Data

US 2014/0316191 A1 Oct. 23, 2014

Related U.S. Application Data

(60) Provisional application No. 61/813,037, filed on Apr. 17, 2013.

(51) Int. Cl.
*A61M 21/02* (2006.01)
*A61B 5/0205* (2006.01)
(Continued)

(52) U.S. Cl.
CPC ........... *A61M 21/02* (2013.01); *A61B 5/0205* (2013.01); *A61B 5/02055* (2013.01); *A61B 5/0476* (2013.01); *A61B 5/0482* (2013.01); *A61B 5/486* (2013.01); *G06F 3/011* (2013.01);
*A61B 5/01* (2013.01); *A61B 5/015* (2013.01); *A61B 5/02438* (2013.01); *A61B 5/0488* (2013.01); *A61B 5/0816* (2013.01); *A61B 5/11* (2013.01); *A61B 5/6803* (2013.01);
(Continued)

(58) Field of Classification Search
CPC .................. A61M 21/00; A61M 21/02; A61M 2021/005; A61M 2021/0083; A61M 2021/0088
USPC ...................................................... 600/26–28
See application file for complete search history.

(56) References Cited

U.S. PATENT DOCUMENTS

| 5,807,114 A * | 9/1998 | Hodges | A61M 21/00 434/219 |
| 7,128,577 B2 * | 10/2006 | Renaud | G09B 23/28 434/236 |
| 2011/0213197 A1 * | 9/2011 | Robertson | A61B 5/486 600/27 |

OTHER PUBLICATIONS

De Zambotti et al., U.S. Appl. No. 61/813,037, "Promoting Sleep in a Virtual Reality Environment," filed Apr. 17, 2013, 7 pages.
(Continued)

*Primary Examiner* — Samuel Gilbert
(74) *Attorney, Agent, or Firm* — Hickman Palermo Becker Bingham LLP

(57) ABSTRACT

Biofeedback virtual reality sleep assistant technologies monitor one or more physiological parameters while presenting an immersive environment. The presentation of the immersive environment changes over time in response to changes in the values of the physiological parameters. The changes in the presentation of the immersive environment are configured using biofeedback technology and are designed to promote sleep.

48 Claims, 6 Drawing Sheets

(51) Int. Cl.
| | |
|---|---|
| A61B 5/0476 | (2006.01) |
| A61B 5/00 | (2006.01) |
| A61B 5/0482 | (2006.01) |
| G06F 3/01 | (2006.01) |
| A61B 5/0488 | (2006.01) |
| A61M 21/00 | (2006.01) |
| A61B 5/01 | (2006.01) |
| A61B 5/024 | (2006.01) |
| A61B 5/08 | (2006.01) |
| A61B 5/11 | (2006.01) |

(52) U.S. Cl.
CPC .......... *A61B 5/6804* (2013.01); *A61B 5/7475* (2013.01); *A61M 2021/005* (2013.01); *A61M 2021/0027* (2013.01); *A61M 2230/005* (2013.01); *A61M 2230/06* (2013.01); *A61M 2230/10* (2013.01); *A61M 2230/42* (2013.01); *A61M 2230/50* (2013.01); *A61M 2230/60* (2013.01); *G06F 2203/011* (2013.01); *G06F 2203/013* (2013.01); *G06F 2203/015* (2013.01)

(56) References Cited

OTHER PUBLICATIONS

Virtual Reality, http://www.vrs.org.uk/virtual-reality-gear/glasses/how-do-they-work.html, "How Do Virtual Reality Glasses Work?," accessed Jun. 10, 2014.
Virtual Reality, http://www.vrs.org.uk/virtual-reality-gear/tracking.html, "Virtual Reality Tracking Systems," accessed Mar. 18, 2014.
Spelman, J. et al., "Post Deployment Care for Returning Combat Veterans," Journal of General Internal Medicine, vol. 27(9), Sep. 2012, pp. 1200-1209.
Wallace, D. et al., "Insomnia characteristics and clinical correlates in Operation Enduring Freedom/Operation Iraqi Freedom veterans with post-traumatic stress disorder and mild traumatic brain injury: An exploratory study," Journal of Sleep Medicine, vol. 12(9), Oct. 2011, pp. 850-859.
Zeitzer, J. et al., "Insomnia in the context of traumatic brain injury," Journal of Rehabilitation Research and Development, vol. 46(6), Feb. 2009, pp. 827-836.
Ouellet, M. et al., "Insomnia in Patients with Traumatic Brain Injury: Frequency, Characteristics, and Risk Factors,". Journal of Head Trauma Rehabilitation, vol. 21(3), May 2006, pp. 199-212.
McLay, R. et al., "Insomnia is the Most Commonly Reported Symptom and Predicts Other Symptoms of Post-Traumatic Stress Disorder in U.S. Service Members Returning From Military Deployments," Military Medicine, vol. 175, Oct. 2010, pp. 759-762.
Hughes, J. et al., "Insomnia and Symptoms of Post-traumatic Stress Disorder Among Women Veterans," Behavioral Sleep Medicine, vol. 11(4), Sep. 2013, pp. 258-274.
Goldzweig, C.L., et al., "The State of Women Veterans' Health Research: Results of a Systematic Literature Review," Journal of General Internal Medicine, vol. 21(S3), Mar. 2006, pp. 882-S92.
Wright, K., et al., "Insomnia as Predictor Versus Outcome of PTSD and Depression Among Iraq Combat Veterans," Journal of Clinical Psychology, vol. 67(12), Dec. 2011, pp. 1240-1258.
Fortier-Brochu, E., et al., "Insomnia and daytime cognitive performance: A meta-analysis," Sleep Medicine Reviews, vol. 16(1), Feb. 2012, pp. 83-94.
Spiegelhalder, K., et al., "The association between insomnia and cardiovascular diseases," Nature and Science of Sleep, vol. 2, May 2010, pp. 71-78.
Bonnet, M. et al., "Hyperarousal and insomnia: State of the science," Sleep Medicine Reviews, vol. 14(1), Feb. 2010, pp. 9-15.
Riemann, D. et al., "The treatments of chronic insomnia: A review of benzodiazepine receptor agonists and psychological and behavioral therapies," Sleep Medicine Reviews, vol. 13(3), Jun. 2009, pp. 205-214.

Schoenfeld, F. et al., "Treatment of sleep disturbances in post-traumatic stress disorder: A review," Journal of Rehabilitation Research and Development, vol. 49(5), Jul. 2012, pp. 729-752.
Rizzo, A., et al., "Virtual Reality Goes to War: A Brief Review of the Future of Military Behavioral Healthcare," Journal of Clinical Psychology in Medical Settings, vol. 18(2), Jun. 2011, pp. 176-187.
Rose, F., et al., "Virtual Reality in Brain Damage Rehabilitation: Review," Cyberpsychology and Behavior, vol. 8(3), Jun. 2005, pp. 241-262.
Gerardi, M., et al., "Virtual Reality Exposure Therapy for Post-Traumatic Stress Disorder and Other Anxiety Disorders," Current Psychiatry Reports, vol. 12(4), Aug. 2010, pp. 298-305.
McLay, R., et al., "Development and Testing of Virtual Reality Exposure Therapy for Post-Traumatic Stress Disorder in Active Duty Service Members Who Served in Iraq and Afghanistan," Military Medicine, vol. 177(6), Jun. 2012, pp. 635-642.
Malloy, K. et al., "The effectiveness of virtual reality distraction for pain reduction: a systematic review," Clinical Psychology Review, vol. 30(8), Dec. 2010, pp. 1011-1018.
Rizzo, A. et al., "A SWOT Analysis of the Field of Virtual Reality Rehabilitation and Therapy," Presence: Teleoperators & Virtual Environments, vol. 14(2), Apr. 2005, pp. 119-146.
Everly Jr., G. et al., "Biofeedback in the Treatment of the Stress Response," A Clinical Guide to the Treatment of the Human Stress Response, Dec. 2012, pp. 267-291.
Epstein, D., et al., "Insomnia treatment acceptability and preferences of male Iraq and Afghanistan combat veterans and their healthcare providers," Journal of Rehabilitation Research and Development, vol. 49(6), Aug. 2012, pp. 867-878.
Kumar, R., et al., "Implementation of an Augmented Reality System for Training Dismounted Warfighters," the Interservice/Industry Training, Simulation & Education Conference (I/ITSEC), Dec. 2012, 12 pages.
Oskiper, T., et al., "Multi-sensor navigation algorithm using monocular camera, IMU and GPS for large scale augmented reality," Mixed and Augmented Reality (ISMAR), 2012 IEEE International Symposium, Nov. 2012, pp. 71-80.
AppAdvice, https://itunes.apple.com/US/app/id337349999?mt=8, "Deep Sleep with Andrew Johnson", Michael Scheider, accessed Jun. 9, 2014.
AppAdvice, https://itunes.apple.com/us/app/asleep/id286538618?mt=8, "aSleep", Signs Studio, accessed Jun. 9, 2014.
AppAdvice, https://itunes.apple.com/US/app/id341324632?mt=8, "Pzizz Sleep", Pzizz Technology Limited, accessed Jun. 9, 2014.
AppAdvice, https://itunes.apple.com/US/app/id337291691?mt=8, "Long Deep Breathing", Tech 2000 Inc., accessed Jun. 9, 2014.
AppAdvice, https://itunes.apple.com/US/app/id320606217?mt=8, "Sleep Cycle Alarm Clock", Northcube AB, accessed Jun. 9, 2014.
SensorTower, https://sensortower.com/ios/at/vanke-software-inc/app/esleep-lite/308286611, "Esleep Lite", accessed Jun. 9, 2014.
AppAdvice, https://itunes.apple.com/US/app/id328349387?mt=8, "Proactive Sleep Alarm Clock", Proactive Life LLC, accessed Jun. 9, 2014.
AppAdvice, https://itunes.apple.com/US/app/id354176883?mt=8, "Relax & Rest Guided Mediations", Meditation Oasis, accessed Jun. 9, 2014.
AppAdvice, https://itunes.apple.com/us/app/alarm-tunes-music-alarm-clock/id496115975?mt=8, "Alarm Tunes—Music Alarm Clock", McLean Mobile Solutions, Inc., accessed Jun. 9, 2014.
Healthline, http://www.healthline.com/health-slideshow/top-insomnia-iphone-android-apps#1, "The Best Sleep iPhone & Android Apps of the Year", Kenneth R. Hirsch, M.D., accessed Jun. 9, 2014.
Hamdan et al., "A Biofeedback System for Sleep Management", University of Ottawa, dated Nov. 16, 2012, IEEE, 5 pages.
Manber, R. et al., "Sex Differences in Sleep and Sleep Disorders: A Focus on Women's Sleep" International Journal Sleep Disorders, vol. 1, dated Jan. 2008, pp. 7-15.
C. Zayfert, J. DeViva, "Residual Insomnia Following Cognitive Behavioral Therapy for PTSD," Journal of Trauma Stress, Feb. 2004; vol. 17, Issue 1: pp. 69-73.; 5pgs.

(56) References Cited

OTHER PUBLICATIONS

B. Krakow et al., "Sleep disturbances and suicidal ideation in sleep medical center patients," Preliminary communication, Journal of Affective Disorders, published Jan. 6, 2011, 131: pp. 422-427; 2011 Elsevier B.V.; 6pgs.

Morin, Dr. Charles Benca, Ruth, "Chronic Insomnia," DOI: http://dx.doi.org/10.1016/S0140-6736(11)60750-2, Jan. 20, 2012; published in The Lancet, vol. 379, No. 9821, p. 1129-1141; Mar. 24, 2012; http://www.thelancet.com/journals/lancet/article/PIIS0140-6736(11)60750-2/fulltext; 13pgs.

Edinger, J. D., et al., "Cognitive-behavioral therapy for primary insomnia," Clinical Psychology Review, 25 (2005), pp. 539-558; published by Elsevier Ltd.; doi:10.1016/j.cpr.2005.04.003; 20pgs.

* cited by examiner

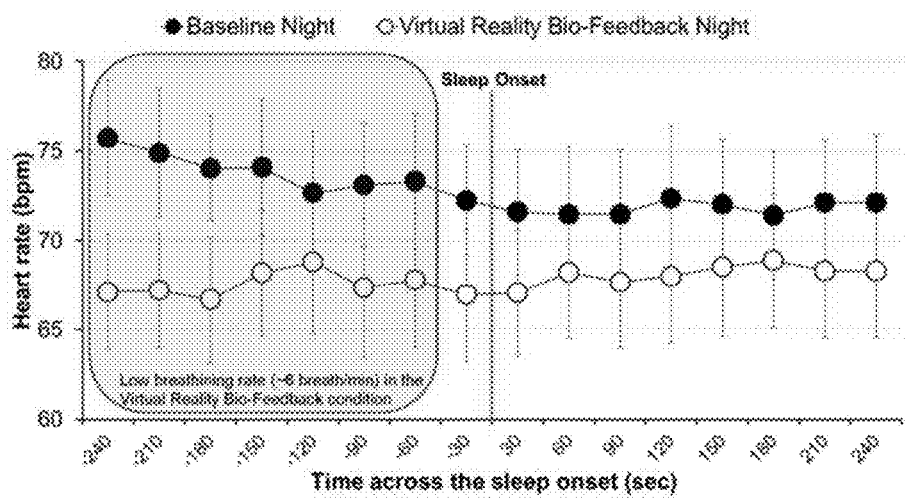
FIG. 7
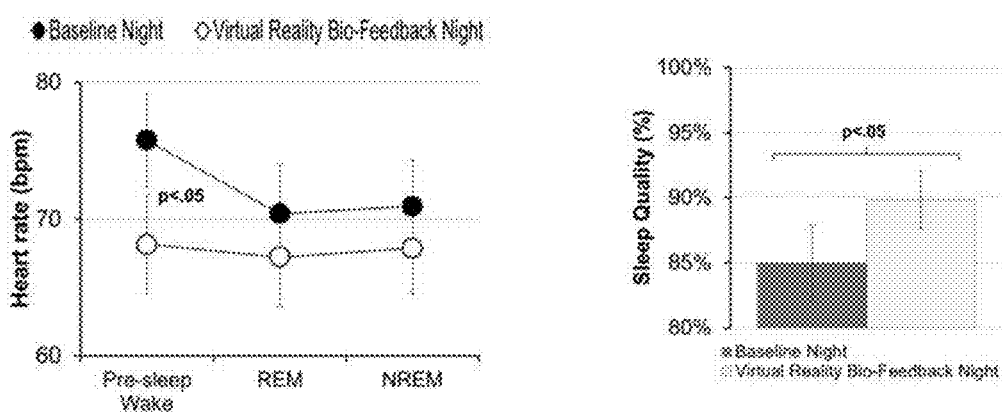
FIG. 8
FIG. 9

BIOFEEDBACK VIRTUAL REALITY SLEEP ASSISTANT

CROSS-REFERENCE TO RELATED APPLICATION

This application claims priority to and the benefit of U.S. Provisional Patent Application Ser. No. 61/813,037, filed Apr. 17, 2013, which is incorporated herein by this reference.

BACKGROUND

Insomnia is the most common sleep disorder. Insomnia is considered a hyper-arousal disorder in which both cognitive and physiological domains are over-activated. Research has shown that insomnia is associated with elevated autonomic nervous system activation, particularly at sleep onset, which can adversely impact a person's health and wellbeing in a number of ways. Sleep onset in insomniacs is characterized by high levels of cognitive activity, worry, rumination and intrusive thoughts that, together with the autonomic hyper-activation, impede the onset of sleep. Predisposing factors that can increase a person's vulnerability to insomnia include age, gender, coping strategy, personality traits, and genetic factors. Insomnia can be triggered by acute stressful events, such as illness or trauma; it can be a chronic disorder without specific cause, or can be a symptom of other disorders. Perpetuating factors, such as the use of caffeine or alcohol, excessive worry, and irregular wake/sleep schedules, may contribute to the development and persistence of insomnia.

Cognitive-Behavioral Therapy (CBT) and pharmacotherapy are two main lines of treatment that are currently available for insomnia. However, many insomnia sufferers do not wish to use pharmacotherapy and there is limited availability of CBT.

BRIEF DESCRIPTION OF THE DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

FIGS. 7-9 are simplified plots of illustrative test results obtained during the use of at least one embodiment of the sleep assistant of FIG. 1.

DETAILED DESCRIPTION OF THE DRAWINGS

Figure 1:
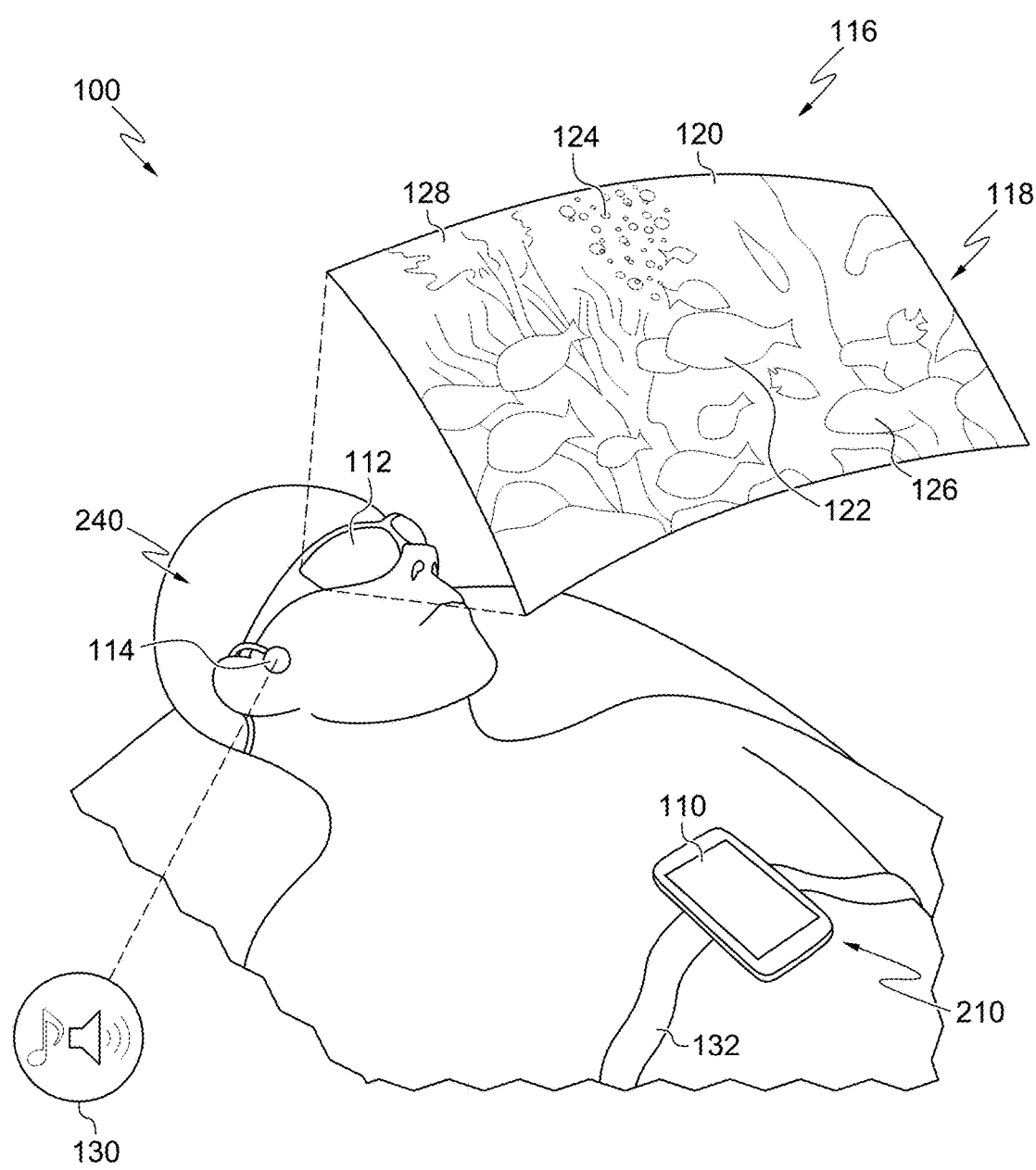
FIG. 1 is a simplified depiction of a person using an embodiment of a biofeedback virtual reality sleep assistant as disclosed herein.

While the concepts of the present disclosure are susceptible to various modifications and alternative forms, specific embodiments thereof are shown by way of example in the drawings and are described in detail below. It should be understood that there is no intent to limit the concepts of the present disclosure to the particular forms disclosed. On the contrary, the intent is to cover all modifications, equivalents, and alternatives consistent with the present disclosure and the appended claims.

Insomniacs are characterized by elevated levels of physiological arousal (e.g. high heart rate, elevated high frequency electroencephalographic activity) together with cognitive hyperactivation (e.g. anxiety, worry, rumination, intrusive thoughts), particularly at sleep onset. Also, for many insomniacs, the bed and bedroom can become associated with a disturbed sleep pattern. As a result, entry into the familiar bedroom environment can become a conditioned cue that perpetuates and increases the severity of insomnia. As disclosed herein, virtual reality scenarios can be designed to remove individuals from their undesirable sleep environment by immersing them in a new, peaceful and relaxing environment, distracting them from other factors that might contribute to insomnia, such as worry and rumination. Additionally, as disclosed herein, biofeedback techniques can be incorporated into a virtual reality system to promote psychophysiological relaxation (by reducing physiological hyper-arousal) and thus promote their sleep. To do this, some of the disclosed embodiments focus the application of biofeedback and virtual reality techniques at the point in time that is prior to sleep onset. As used herein, "sleep onset period" generally refers to the time period beginning with "lights out," when the person begins the process of trying to fall asleep, and continues up to the point of loss of consciousness, e.g., when the person enters the initial sleep state, which usually occurs before the polysomnography (PSG) sleep onset. After sleep onset, the techniques disclosed herein can be discontinued because the person is no longer conscious of the immersive virtual environment. In other words, some of the disclosed embodiments are directed to helping people guide themselves across the sleep onset process to promote the transition from the conscious (awake) to the unconscious level (sleep). In this way, aspects of the disclosed embodiments apply biofeedback and virtual reality techniques to make the process of falling asleep easier.

Figure 2:
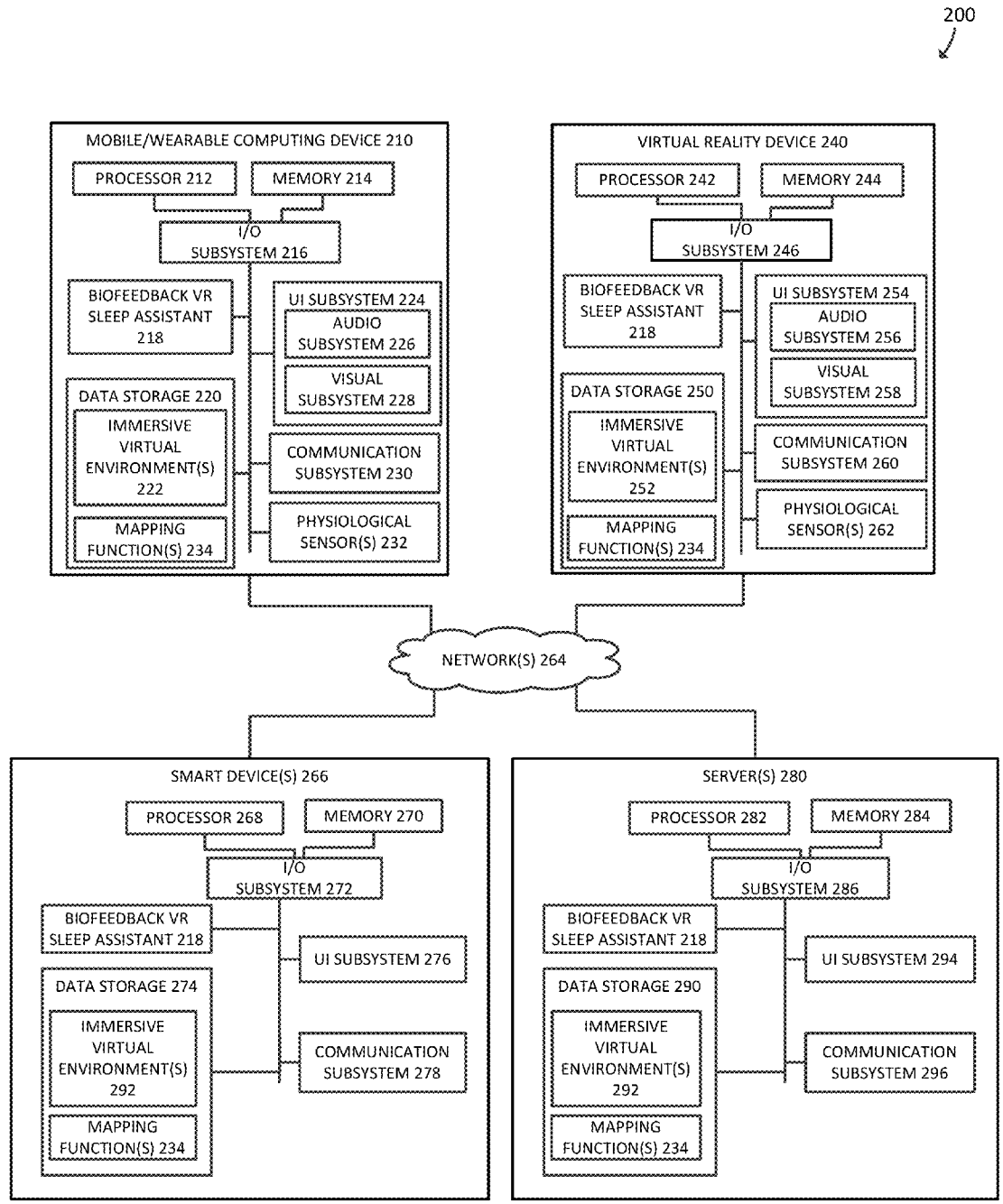
FIG. 2 is a simplified block diagram of at least one embodiment of a computing environment for the sleep assistant of FIG. 1.

Referring now to FIGS. 1 and 2, an embodiment of a biofeedback virtual reality system 100 includes a virtual reality device 240 and a wearable sensor device 210. The device 210 may be embodied as a mobile computing device, as shown in FIG. 1, or as a wearable smart-sensor (e.g. an IMU or inertial measurement unit) that communicates wirelessly with a mobile computing device (such as a smart phone lying on a table next to the person). In other words, the device 210 may include two parts: [1] a wearable sensor and [2] a mobile computing device (where the mobile computing device is a separate device from the sensor and may interface with the sensor by wireless (e.g., by WIFI, BLUETOOTH, or other suitable wireless or optical communication technology), or may include one part (e.g., a mobile computing device with an integrated sensor). The mobile computing device and/or the smart-sensor communicates wirelessly with the virtual reality device 240 (e.g., eye wear and headphones). The virtual reality device 240 immerses a person in a virtual reality environment 116. The wearable smart sensor together with the mobile computing device 210 operates a sleep assistant computer application 218 that applies biofeedback technology to the presentation of the immersive virtual environment 116, in order to target a state of hyper-arousal (or hyper-activation) being experienced by the person using the system 100 ("user"). The system 100 creates a positive biofeedback loop in which the virtual reality device 240 provides cognitive relaxation/distraction and the biofeedback technology embodied in the sleep assistant application 218 promotes sleep by providing positive feedback (by modulating the degree of immersion in the virtual environment 116) in response to physiological signals indicating the user's current level of relaxation. Using the biofeedback technology, the system 100 presents increasingly immersive virtual reality environments as the user produces the desired level of physiological activation, and then modulates the virtual environment so as not to disturb the person once they have fallen asleep. Alternatively or in addition to presenting the immersive virtual reality environments, the system 100 can control various aspects of the user's surrounding physical (real-world) environment, in response to the biofeedback signals. For instance, the system 100 can communicate with various smart devices in the room, such as devices that provide or reduce ambient lighting, including an alarm clock, shades, and/or other devices, to reduce distractions that may be introduced by such devices. For example, the system 100 can use the biofeedback signals (e.g., the user's breathing rate) to automatically change an aspect of the user's physical environment; e.g., if the user slows down his or her breathing rate, the system 100 may decrease the brightness of the room. The immersive environment 116 is "virtual" in the sense that it includes computer-synthesized elements that are presented to the user in place of or in conjunction with the real-world environment. As used herein, "virtual reality" or "VR" may refer to, among other things, virtual reality, augmented reality, enhanced reality, and/or other types of interactive or non-interactive computer-generated immersive user experiences. For example, in some embodiments, the immersive virtual environment 116 may include a visual display 118 that presents a series of animated two- or three-dimensional visual elements (e.g., graphical elements 122, 124, 126, 128) against a relatively static graphical backdrop (e.g., element 120), and the person experiences the visual display 118 passively (e.g., by viewing only). In other embodiments, the system 100 may allow the user to interact with the elements presented in the visual display 118 (e.g., via an "avatar" or by the user directly navigating in the scenario using, for instance, gaze, gestures or pointing devices). For instance, the system 100 may permit the user to move objects around in the virtual environment, or to interact with or insert themselves into the virtual environment as an avatar. As an example, a "sleep mask" configured as a virtual reality device 240 can detect the user's gaze and move the avatar in the same direction as the user's gaze allowing the user to navigate in the virtual environment moving his eyes. As another example, the system 100 may change the point of view or focus, or zoom in or zoom out in a particular direction, in response to the user's gestures or other body movements, or may rotate, pan, or otherwise adjust the virtual scene in response to a characteristic of the person's gaze (e.g., gaze direction, pupil dilation, etc.), or in response to other detected bio-signals (e.g., reduction in muscle activity). Using the bio-feedback mechanism, the user is an active participant in controlling the virtual environment and synthesized sounds. In general, a greater physiological relaxation (as promoted by the sleep assistant 218) leads to a more pleasant environment (e.g., increased immersion in the virtual reality) and thus promotes more cognitive relaxation/distraction. The sleep assistant 218 responds to increased physiological relaxation (as detected by, e.g., a reduction in breathing rate) by increasing the degree of virtual immersion (by providing, for example, pleasant/relaxing sounds, more visual elements in the immersive environment that increase the user's "sense of presence" in the immersive environment), etc. The increased degree of virtual immersion then leads to even greater cognitive relaxation/distraction (e.g. the person is now fully immersed in a virtual environment and he/she forgot all worries, ruminations, etc.), which promotes sleep.

The virtual environment 116 is immersive in the sense that it is designed to attract the user's attention by increasing the user's sense of presence in a virtual world and by removing distractions that may occur in the surrounding real-world scene, e.g., by occluding the background and/or restricting the user's peripheral vision. The system 100 may achieve the immersive nature of the virtual environment 116 by presenting the visual display 118, playing an audio soundtrack 130, presenting a combination of the visual display 118 and the audio soundtrack 130, and/or providing other sensory stimuli. In all embodiments, the level of brightness of the visual stimulation provided by the visual display 118 is low, in order to avoid any alterations in hormone production (e.g. to avoid changes in melatonin).

The illustrative immersive virtual environment 116 includes a combination of visual 118 and audio 130 stimuli, but other embodiments may include other types of sensory stimuli, such as tactile, temperature, taste, smell, and others, alternatively or in addition to the visual 118 and audio 130 stimuli. For example, some embodiments of the virtual environment 116 only include visual stimuli while other embodiments only include audio stimuli. The system 100 coordinates the presentation of the various sensory stimuli with physiological information in real time to create a state of relaxation in the person experiencing the immersive virtual environment 116. For example, as explained further below, the system 100 may increase or decrease any of a number of features of any of the sensory stimuli, or selectively turn different sensory stimuli on and off, over time in response to changes in the person's physiological parameters. As used herein, "in real time" may refer to, among other things, the fact that an automated biofeedback process occurs in response to sensed physiological information about the person using the system 100, during a period in which the person is using the system 100. In other words, the illustrative system 100 changes one or more aspects of the immersive virtual environment 116 directly in response to changes in the sensed physiological information, using biofeedback technology based on user actions that is designed to promote sleep. To do this, the mobile/wearable computing device 210 and/or the virtual reality device 240 analyze one or more physiological parameters that are obtained or derived from sensor signals. As used herein, "physiological parameters" may refer to, among other things, breathing rate (respiration rate) (e.g., breaths per minute), heart rate (e.g., beats per minute), brain activity (e.g. electroencephalographic signals), body movements, muscle activity; or any other type of measurable human physiological activity, or any combination of the foregoing. Using biofeedback technology, the system 100 modifies the immersive virtual environment 116 in response to changes in the physiological parameters in a manner that is designed to guide the person away from the state of hyper-arousal and toward a state of sleep.

Different physiological parameters may have different roles in modifying the various aspects of the virtual environment (e.g., breathing rate can guide the speed of the navigation in the virtual environment whereas the muscle tone may guide the density of the virtual elements presented in the immersive environment 116). As an example, if the user decreases his or her breathing rate, the system 100 can reduce the speed of the fish swimming in an aquatic scene (but not change other aspects of the environment 116); and if, at the same time, the user reduces his or her muscle activity, the system 100 can increase the number of fish swimming in the visual scene. Thus, different physiological parameters can be linked with different aspects of the immersive scenario 116 using feedback on different bio-signals, in order to potentially increase the user's relaxation.

Referring now to FIG. 1 in more detail, the illustrative visual display 118 is embodied as a three-dimensional (3D) display of visual elements. In the illustration, the visual elements depict an aquatic scene and include a background 120 (e.g., water), a background element 128 (e.g., coral), and a number of foreground elements 122 (e.g., fish), 124 (air bubbles), 126 (e.g., rocks). The system 100 can adjust the presentation of any of the visual elements 120, 122, 124, 126, 128, or add or remove visual elements, in response to changes in physiological parameters. Further, each of the visual elements has a number of features, including speed (e.g., the rate at which the element moves across the display), quantity (e.g., the number of elements of a certain type presented on the display), density (e.g., the number of elements presented in a certain area of the display), frequency (e.g., the rate at which elements of a certain type are presented), color, brightness, contrast, direction of movement, depth (in 3D), focus (e.g. clarity), point of view, and/or complexity (e.g., amount of finer-grain details depicted in the element). The system 100 can modify any of these and/or other features of the visual elements depicted in the visual display 118, based on the user's physiological parameters. Of course, while the visual display 118 depicts an aquatic scene, any type of visual display that is designed or selected to promote sleep may be used. For example, an ocean, sky, or forest scene may be used, or the visual display 118 may be configured according to the preferences of a particular user of the system 100. In FIG. 1, it should be understood that in operation, the visual display 118 is actually displayed in the virtual reality viewing glasses 112, but is shown as projected in order to better illustrate the details described above.

The illustrative audio soundtrack 130 includes a number of audio elements, which may include various types of sounds (e.g., spoken words, music, nature sounds, etc.) or a combination thereof. In the illustration, the audio elements are sounds that are coordinated with the visual display 118 (e.g., water flowing and bubbling sounds); however, the audio soundtrack can include any type of audio selected or configured to promote sleep, including selections from the user's digital music library. The system 100 can adjust the presentation of any of the audio elements, or add or remove audio elements, in response to changes in physiological parameters. Each of the audio elements has a number of features, including volume, content (e.g., words, sounds, and/or music), speed (e.g., tempo), complexity (e.g., number of different types or layers of sound), degree of "surround sound," and/or intensity (e.g., acoustic intensity). The system 100 can modify any of these and/or other features of the audio elements 130 based on the user's physiological parameters.

The illustrative wearable smart-sensor and mobile computing device 210 includes a computing device 110 (e.g., a smartphone, a tablet computer, an attachable/detachable electronic device such as a clip-on device, a smart watch, smart glasses, a smart wristband, smart jewelry, and/or smart apparel) and a positioner 132 (e.g., a strap, tether, clip, VELCRO® tab, etc.). However, any type of computing device that includes a processor and memory and can interact with the virtual reality device 240 in a relatively non-intrusive manner (e.g., without causing discomfort to the person using the system 100) may be used as the computing device 110.

The positioner 132 is configured to secure the mobile or wearable computing device 210 in a position in which a sensor 232 (FIG. 2) of the device 210 can detect the user's physiological activity and generate physiological signals representing the user's physiological activity. However, the positioner 132 may be omitted, in some embodiments. Additionally, the sensors used to detect the user's physiological activity do not need to be attached to or worn by the person. For example, the physiological sensor 232 can be incorporated in the person's bed or mattress, or into a mattress pad or bed linens (e.g., a fitted sheet). Additional details of the mobile or wearable computing device 210 are described below with reference to FIG. 2.

The illustrative virtual reality device 240 includes a visual display system 112 and an audio delivery system 114. The illustrative visual display system 112 is embodied as commercially available virtual reality eyewear. Other embodiments of the visual display system 112 utilize other types of visual display systems, such as high-definition video glasses, non-rigid sleep masks adapted for virtual reality, televisions, projection systems (to project a display of visual elements onto a wall or ceiling), or holograms.

The illustrative audio delivery system 114 is embodied as commercially available bone-conducting headphones. Other embodiments of the audio delivery system 114 use other methods of audio delivery, such as conventional audio headphones (e.g., earbuds), three-dimensional (3D) surround sound systems, remote speakers, indoor waterfall systems or fountains, and/or other electronically-controllable noise-making devices. In general, the components of the system 100 are in communication with each other as needed by suitable hardware and/or software-based communication mechanisms, which may be enabled by an application programming interface, operating system components, a network communication subsystem, and/or other components. Additional details of the virtual reality device 240 are described below with reference to FIG. 2.

Referring now to FIG. 2, a simplified block diagram of an exemplary computing environment 200 for the computing system 100 is shown. The illustrative environment 200 includes the mobile or wearable computing device 210 and the virtual reality device 240, which are in communication with one or more smart devices 266 and/or one or more server computing devices 280 via one or more networks 264. The biofeedback VR sleep assistant 218 is, illustratively, embodied as a distributed application including "front end"

components that are local to each of the devices 210, 240, 270 and including "back end" portions that reside on the server(s) 280 (e.g., "in the cloud"). Similarly, a library or searchable database of selectable immersive virtual environments 116 may be distributed across the network 270. For example, the immersive virtual environments 222, 252, 292 may include a number of different virtual environments 116, or copies or portions of particular virtual environments 116. Further, other portions of the system 100 may be distributed on various devices 210, 240, 280 across the network 270, such as mapping functions 234. In other embodiments, however, the sleep assistant 218, the mapping function(s) 234, and the immersive virtual environment(s) 222, 252, 292 may be stored entirely on the mobile or wearable computing device 210 or entirely on the virtual reality device 240. In some embodiments, portions of the sleep assistant 218, the mapping function(s) 234 or the immersive virtual environment(s) 222, 252, 292 may be incorporated into other systems or interactive software applications. Such applications or systems may include, for example, operating systems, middleware or framework (e.g., application programming interface or API) software, and/or user-level applications software.

The mobile or wearable computing device 210 may be embodied as any type of computing device that is capable of performing the functions described herein (e.g., modulating the presentation of the immersive virtual environment 116 based on physiological signals). In some embodiments, the devices 210, 240 may be integrated as a unitary device. Such a unitary device may also include one or more physiological sensors 232, 262.

The illustrative mobile or wearable computing device 210 includes at least one processor 212 (e.g. a controller, microprocessor, microcontroller, digital signal processor, etc.), memory 214, and an input/output (I/O) subsystem 216. Although not specifically shown, embodiments of the processor 212 may include separate baseband and applications processors. Features of the baseband and applications processors may be located on the same or different hardware devices (e.g., a common substrate). The baseband processor interfaces with other components of the mobile or wearable computing device 210 and/or external components to provide, among other things, wireless communication services, such as cellular, BLUETOOTH, WLAN, and/or other communication services. In general, the applications processor handles processing required by software and firmware applications running on the mobile or wearable computing device 210, as well as interfacing with various sensors and/or other system resources. However, it should be understood that features typically handled by the baseband processor may be handled by the applications processor and vice versa, in some embodiments.

Although not specifically shown, it should be understood that the I/O subsystem 216 typically includes, among other things, an I/O controller, a memory controller, and one or more I/O ports. The processor 212 and the I/O subsystem 216 are communicatively coupled to the memory 214. The memory 214 may be embodied as any type of suitable computer memory device (e.g., volatile memory such as various forms of random access memory).

The I/O subsystem 216 is communicatively coupled to a number of components, including a user interface subsystem 224. The user interface subsystem 224 includes one or more user input devices (e.g., a microphone, a touchscreen, keyboard, virtual keypad, etc.) and one or more output devices (e.g., audio speakers, displays, LEDs, etc.). The I/O subsystem 216 is also communicatively coupled to a data storage device 220, a communications subsystem 230, and the physiological sensor(s) 232, as well as the biofeedback VR sleep assistant 218. The data storage device 220 may include one or more hard drives or other suitable persistent data storage devices (e.g., flash memory, memory cards, memory sticks, and/or others). The physiological sensing devices 232 may include motion sensors, pressure sensors, kinetic sensors, temperature sensors, biometric sensors, and/or others, and may be integrated with or in communication with the mobile or wearable computing device 210. For example, the sensing device 232 may be embodied as an inertial measurement unit (IMU) sensor of the mobile or wearable computing device 210, and as such may include a multiple-axis gyroscope and a multiple-axis accelerometer. In some embodiments, a respiratory effort sensor, such as a piezo sensor band or a respiratory transducer, may be in communication with or embodied in the computing device 210, alternatively or in addition to the IMU.

Portions of the sleep assistant 218, the mapping function(s) 234, and the immersive virtual environment(s) 222 reside at least temporarily in the data storage device 220. For example, the virtual environments 222 may include a subset of the library of virtual environments 292, where the subset 222 has been selected by the user or provided as part of a base configuration of the sleep assistant 218 or the computing device 210. Portions of the sleep assistant 218, the mapping function(s) 234, and the immersive virtual environment(s) 222 may be copied to the memory 214 during operation of the mobile or wearable computing device 210, for faster processing or other reasons.

The communication subsystem 230 may communicatively couple the mobile or wearable computing device 210 to other computing devices and/or systems by, for example, a cellular network, a local area network, wide area network (e.g., Wi-Fi), personal cloud, virtual personal network (e.g., VPN), enterprise cloud, public cloud, Ethernet, and/or public network such as the Internet. The communication subsystem 230 may, alternatively or in addition, enable shorter-range wireless communications between the mobile or wearable computing device 210 and other computing devices (such as the virtual reality device 240), using, for example, BLUETOOTH and/or Near Field Communication (NFC) technology. Accordingly, the communication subsystem 230 may include one or more optical, wired and/or wireless network interface subsystems, cards, adapters, or other devices, as may be needed pursuant to the specifications and/or design of the particular mobile or wearable computing device 210. Additionally, the communication subsystem 230 may include a telephony subsystem, which enables the computing device to provide telecommunications services (e.g., via the baseband processor). The telephony subsystem generally includes a longer-range wireless transceiver, such as a radio frequency (RF) transceiver, and other associated hardware (e.g., amplifiers, etc.).

The user interface subsystem 224 includes an audio subsystem 226 and a visual subsystem 228. The audio subsystem 226 may include, for example, an audio CODEC, one or more microphones, and one or more speakers and headphone jacks. The visual subsystem 228 may include, for example, personal viewing glasses, projection devices, holograms, televisions, liquid crystal display (LCD) screens, light emitting diode (LED) screens, or other visual display devices. The one or more physiological sensor(s) 232 initially detect the user's "baseline" physiological parameters (e.g., the user's actual measured parameters at the beginning of a sleep promotion session). Once the user's baseline condition or "physiological status" is established, the system 100 presents an initial immersive virtual environment 116 and enters "feedback mode," in which the sensor(s) 232 periodically detect the physiological responses of the user to the presented immersive virtual environment 116, and provide the sleep assistant 218 with physiological signals that can be used by the sleep assistant 218 to determine the user's state of relaxation as it changes over time. The physiological signals output by the sensor(s) 232 may include signals that represent respiration rate, heart rate, brain activity (e.g. electroencephalogram (EEG)), body temperature, and/or other physiological parameters. For example, the sensor 232 may be embodied as an IMU built into the computing device 210 or the virtual reality device 240, which is used to measure the user's breathing rate by detecting the rise and fall of the user's chest or abdomen over time during normal respiration.

In other embodiments, the physiological sensor 232 can include measurement tools that are external to the computing device 210 but which are in communication with the device 210. An example of an external physiological sensor 232 is "textile electrodes," which are formed by knitting or weaving conductive fibers into apparel or garments. Textile electrodes can pick up signals from the heart and other muscles. The physiological activity sensed by the textile electrodes are transmitted through the conductive fibers that are woven into the garment to a processing unit, which then passes the received signals to the mobile or wearable computing device 210, generally through a wireless data connection.

Referring now to the virtual reality device 240 of FIG. 2, the virtual reality device 240 may be embodied as any type of device that is capable of performing the functions described herein (e.g., presenting the immersive virtual environment 116 to the user). To do this, the illustrative virtual reality device 240 is equipped with an audio subsystem 256 and a visual subsystem 258, which may be embodied similarly to the audio subsystem 226 and the visual subsystem 228 described above. Accordingly, the virtual reality device 240 may be embodied with components similar to those of the mobile or wearable computing device 210. For example, in some embodiments, the virtual reality device 240 has a processor 242, memory 244, and an I/O subsystem 246 similar to the mobile or wearable computing device 210. In general, elements of the virtual reality device 240 having the same or similar name as elements of the mobile or wearable computing device 210 may be embodied similarly, and description of those elements is not repeated here. While not specifically shown in FIG. 2, it should be understood that the virtual reality device 240 may include other components as needed to control or provide other various forms of sensory stimuli, such as an ambient temperature controller subsystem, an aroma subsystem, and/or an air movement subsystem. In some embodiments, the virtual reality device 240 is comprised of separate devices. For example, wearable personal viewing glasses and headphone ear buds may be separate components of the virtual reality device 240, or may be integrated into a single device (e.g., GLASS by Google, Inc. or a similar device).

Referring now to the smart device(s) 266 of FIG. 2, the smart device(s) 266 may be embodied as any type of electronic device capable of performing the functions described herein (e.g., controlling an aspect of the user's physical environment). For example, the smart device(s) 266 may include smart lighting, heating, cooling, sound, and/or entertainment systems. The smart device(s) 266 may include components similar to those described above, or may simply include control circuitry to process control signals received from the sleep assistant 218 and adjust a parameter of the device 266 (e.g., light intensity, room temperature, sound volume, etc.). Elements of the smart device(s) 266 having the same or similar name as elements of the mobile or wearable computing device 210 may be embodied in a similar manner and according to the requirements of the particular smart device 266. As such, the description of the similar elements is not repeated here. In the illustrative smart device 266, the virtual sleep assistant 218 is communicatively coupled to I/O subsystem 276, data storage 274, user interface subsystem 276, and communication subsystem 278. Data storage 274 is used to store portions of the mapping function(s) 234 and the immersive virtual environment(s) 292.

Referring now to the server(s) 280 of FIG. 2, the server(s) 280 may be embodied as any type of computing device capable of performing the functions described herein (e.g., storing portions of the immersive virtual environments 292 and/or executing portions of the sleep assistant 218). For example, the server(s) 280 may include components similar to those described above. Elements of the server 280 having the same or similar name as elements of the mobile or wearable computing device 210 may be embodied in a similar manner and according to the requirements of the server 280. As such, the description of the similar elements is not repeated here. In the illustrative server 280, the virtual sleep assistant 218 is communicatively coupled to I/O subsystem 286, data storage 290, user interface subsystem 294, and communication subsystem 296. Data storage 290 is used to store portions of the mapping function(s) 234 and the immersive virtual environment(s) 292.

The computing environment 200 may include other components, sub-components, and devices not illustrated in FIG. 2 for clarity of the description. In general, the components of the environment 200 are communicatively coupled as shown in FIG. 2 by electronic signal paths, which may be embodied as any type of wired or wireless signal paths capable of facilitating communication between the respective devices and components.

Figure 3:
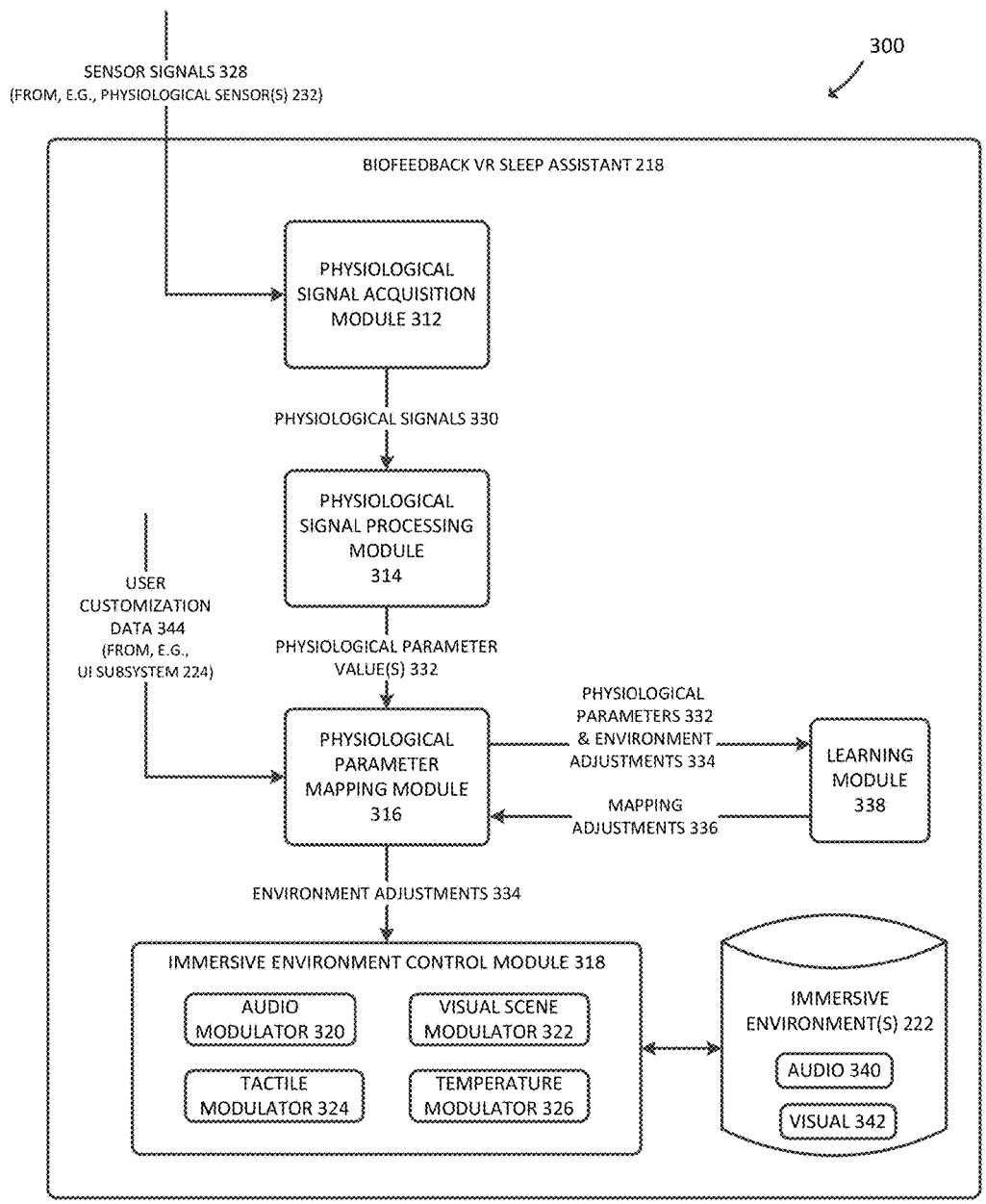
FIG. 3 is a simplified module diagram illustrating an environment of at least one embodiment of the sleep assistant of FIG. 1 in operation.

Referring now to FIG. 3, the biofeedback VR sleep assistant 218 is shown in more detail, in the context of an environment 300 that may be created during the operation of the computing system 100 (e.g., an execution or "runtime" environment). As noted above, the sleep assistant 218 is embodied as a computer application. As used herein, "application" or "computer application" may refer to, among other things, any type of computer program or group of computer programs, whether implemented in software, hardware, or a combination thereof, and includes operating system programs, middleware (e.g., APIs, runtime libraries, utilities, etc.), self-contained software applications, or a combination of any of the foregoing. The sleep assistant 218 is embodied as a number of computerized modules and data structures including a physiological signal acquisition module 312, a physiological signal processing module 314, a physiological parameter mapping module 316, an immersive environment control module 318, a data store including a number of immersive virtual environments 222, and a learning module 338.

The physiological signal acquisition module 312 receives sensor signals 328 from the physiological sensor(s) 232, 262 from time to time during operation of the computing device 210 at a specified sampling rate, which may correspond to a sampling rate performed by the computing device 210. As described above, portions of the sensor signals 328 may reflect human body movements that are indicative of the user's breathing, heartbeat, or other physiological activity.

The signal acquisition module 312 performs standard signal processing techniques (e.g., analog-to-digital conversion, filtering, etc.) to extract the useful information (e.g., measurements of breathing or heart beat activity, brain activity or body temperature) from the sensor signals 328 and outputs the resulting physiological signals 330. In some embodiments, the signal acquisition module 312 is a standard component that is built into the computing device 210. However, the physiological signal acquisition module 312 can also be part of a unit that is external to the computing device 210. For instance, the physiological signal acquisition module 312 can be part of the virtual reality device 240. The physiological signal acquisition module 312 can be communicatively coupled to either the visual subsystem 256 or the audio subsystem 258, in some embodiments. For example, the physiological signal acquisition module 312 may be embodied as a processor in communication with a heart rate monitor that is built into audio earbuds. As another example, the physiological signal acquisition module 312 may be a thermal imager that is remotely placed (with respect to the computing device 210) to periodically measure the body temperature of the user.

The physiological signal processing module 314 receives the physiological signals 330 from the physiological signal acquisition module 312, maps the physiological signals to one or more physiological parameters (e.g., respiration rate, heart rate, etc.), each of which has a range of possible values, and calculates the current data value 332 for each of the physiological parameters. For example, the physiological signal processing module 314 may determine a value of a physiological parameter from one or multiple physiological signals 330, or from one or multiple instances of the same physiological signal 330 over time. The module 314 may execute one or more algorithms to map the physiological signals 330 to physiological parameters or to determine physiological parameter values 332. For example, a robust algorithm based on Fourier analysis may be used to compute the dominant oscillation period from the raw IMU data that is directly related to breathing rate.

The physiological parameter mapping module 316 uses the physiological parameter values 332 to determine the immersive virtual environment 116 that is to be presented to the user. The physiological parameter mapping module 316 maps the physiological parameter values 332 received from the physiological signal processing module 314 to the features of the immersive virtual environment 116. For example, if the immersive virtual environment 116 includes audio and visual stimuli, the physiological parameter value and its mapping determine the features of the audio and visual stimuli to be presented to the user. In some embodiments, the mapping is accomplished by one or more look-up tables that indicate relationships between various physiological parameter values and features of the immersive virtual environment 116. For instance, a look-up table may link a physiological parameter value or range of values to a pre-determined audio volume and number or type of visual elements to display. In other embodiments, a continuous function (e.g., a linear or Gaussian function) may be used to define the mapping. Illustrative examples of mapping tables are shown below in TABLE 1 and TABLE 2.

In some cases, a single physiological parameter value of a single parameter may be used to determine all of the parts of the virtual environment 116 to be presented by the user: for example, both the visual elements and the audio elements. However, the mapping may be defined differently or determined separately for different elements of the virtual environment. For example, a mapping table or mapping function 234 may define relationships between respiration rates and features of the visual display 118, while another mapping table or mapping function 234 may define relationships between the respiration rates and features of the audio soundtrack 130. In other cases, multiple physiological parameters and their corresponding parameter values may be used. For example, one physiological parameter may be used to control the visual display 118 and a different physiological parameter may be used to control the audio 130 or other aspects of the two subsystems. Additionally, different mapping tables or functions 234 may be used to control the smart device(s) 266.

In some embodiments, the mapping table or mapping function used by the parameter mapping module 316 may be customized for a particular user based on user customization data 344. The user customization data 344 may include, for example, user preferences, demographic information, or clinical sleep information specific to the user. As an example, the system 100 may include a number of different parameter mapping tables for different populations of users, and the user customization data 344 may be used to select an appropriate mapping table (based on, e.g., age, gender, or body size). The mapping tables or mapping functions, or portions thereof, may be stored in data storage of any of the devices 210, 2430, 266, 280, as mapping functions 234, or in other data storage locations.

With the parameter input value(s) 332 and the mapping table or function of the parameter mapping module 316, the system 100 determines changes or adjustments to be made to the immersive virtual environment 116 in response to the current parameter value(s) 332. For example, the immersive virtual environment 116 may include a succession of stages, where each stage represents a particular combination of sensory stimuli, and the change or adjustment may include transitioning the presentation to a different stage of the virtual environment 116. The specifications for these changes or adjustments are passed to the immersive environment control module 318 as environment adjustments 334.

In some embodiments, the parameter values 332, corresponding environment adjustments 334, and subsequent parameter values 332 (e.g., a representation of the user's response to the previous environment adjustment 334) (which may be collectively referred to as "training data") are passed to the learning module 338 from time to time. The learning module 338 applies one or more artificial intelligence techniques (such as an unsupervised machine learning algorithm) to the training data to algorithmically learn the user's typical responses to different environment adjustments 334. Based on this learning, the learning module 338 formulates recommended mapping adjustments 336, which indicate modifications to the mapping function that are based on the user's actual behavior over time. The learning module 338 passes the mapping adjustments 336 to the parameter mapping module 316, which updates its mapping table or mapping function based to incorporate the mapping adjustments 336.

In some embodiments, the learning module 338 monitors the physiological signals over the course of a sleep session (e.g., overnight) and outputs feedback (e.g., in the morning) about sleep quality or overall cardiac functioning of the user. Alternatively or in addition, the learning module 338 can make modifications in the selection of the immersive scenario and/or the degree of immersion in subsequent sleep sessions (e.g., for the following night), in response to its assessments of the user's previous sleep quality and/or nocturnal physiology. In this way, the system 100 can, in an automated fashion, learn and change the immersion scenario or settings based on data indicating sleep patterns of a general population (and/or based on a user's individual nocturnal physiology—e.g., cardiac functioning).

The immersive environment control module 318 controls the modifications to the presentation of the immersive virtual environment 116 in response to the physiological signals 330. The immersive environment control module 318 receives the environment adjustments 334, accesses the requisite elements of the immersive environment(s) 222 (which, illustratively, include audio elements 340 and visual elements 342), and constructs a modified version of the virtual environment 116, incorporating the environment adjustments 334. Where the virtual environment 116 includes multiple different types of sensory stimuli, the control module 318 includes a modulator 320, 322, 324, 326 for each different type of stimulus. For example, the audio modulator 320 controls the modification of the presentation of audio elements and their respective features (e.g., volume, content, speed, complexity, intensity, and/or other aspects of the audio soundtrack 130), while the visual scene modulator 322 controls the modification of the presentation of visual elements and their respective features (e.g., object movements, number and type of different objects displayed, color schemes, brightness levels, and/or other aspects of the visual display 118). The tactile modulator 324 and the temperature modulator 326 operate in a similar fashion to control tactile and temperature stimuli, and similar modulators operate similarly for other types of sensory stimuli. In this way, the illustrative immersive environment control module 318 constructs and adjusts the virtual environment 116 "on the fly," e.g., by performing graphics rendering in real time, as opposed to simply selecting and presenting previously created content. The immersive environment control module 318 transmits control signals to the virtual reality device 240 to cause the virtual reality device 240 to present the various adjustments to the virtual environment 116 to the user.

Figure 4:
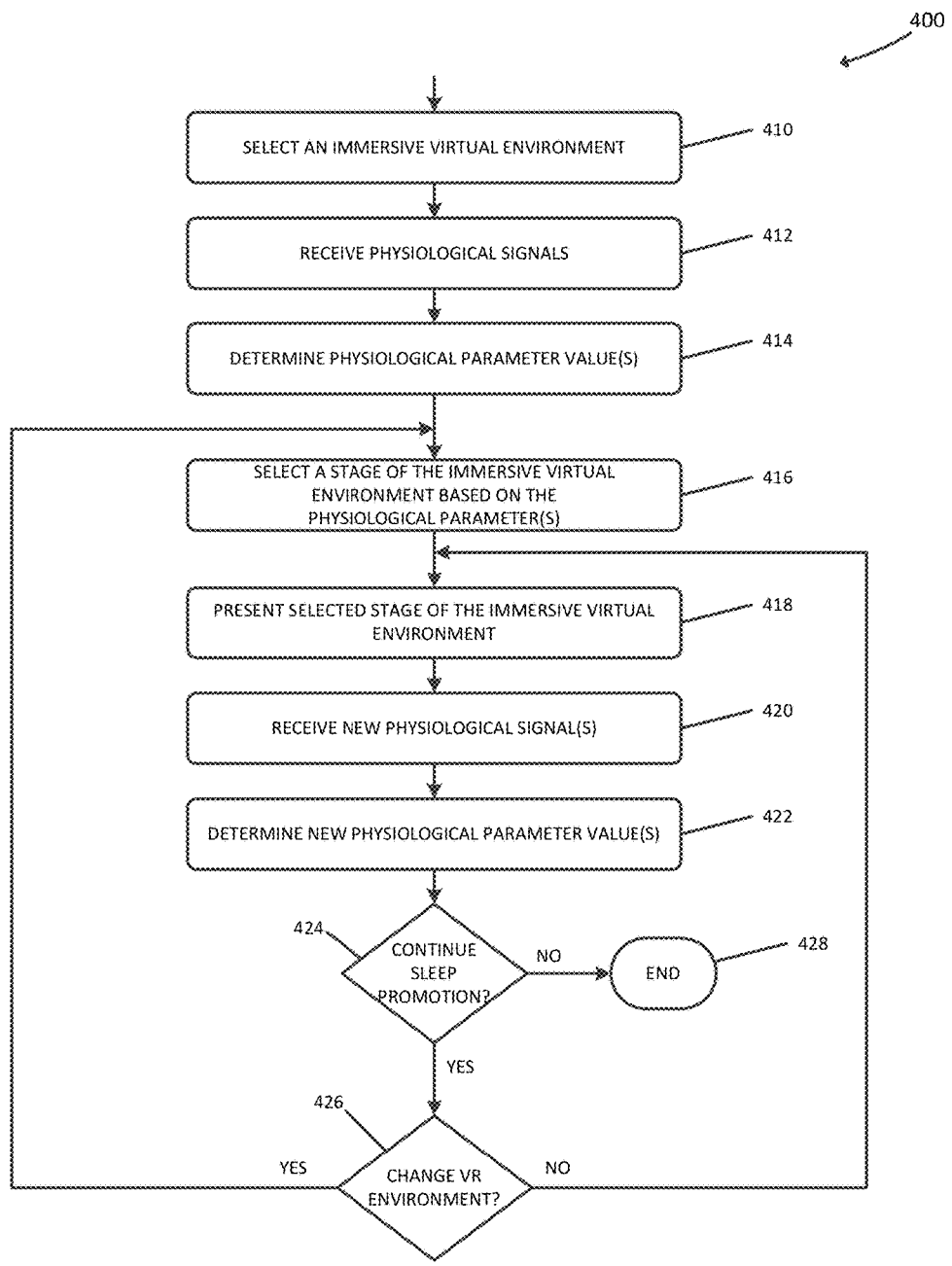
FIG. 4 is a simplified flow diagram of at least one embodiment of a method for promoting sleep with the sleep assistant of FIG. 1.

Referring now to FIG. 4, a flow diagram provides an illustration of a method 400 by which embodiments of system 100 may be used to, for example, conduct a sleep promotion session. The method 400 may be embodied as computerized programs, routines, logic and/or instructions that are executed by the computing system, e.g., the computing device 210 and/or the virtual reality device 240. In FIG. 4, a person attempting to fall asleep, or simply to become more relaxed, uses the system 100 to immerse themselves in a virtual reality environment. For example, the person may be instructed or coached by the sleep assistant 218 to slow his or her breathing rate (or may do so on his or her own) in order to cause the virtual reality environment to become more immersive. In the method 400, a process of presenting an immersive virtual environment that adjusts automatically in response to sensor signals representing physiological activity of the user is performed. Of course, as discussed above, aspects of the user's physical environment (e.g., ambient lighting) can also be adjusted (e.g., by the system 100 interfacing with one or more "smart" devices 266 in the physical environment). Such adjustments to the physical environment may be initiated in conjunction with or separately from the adjustments to the virtual environment. For example, the system 100 may include one or more separate mapping functions 234 that the sleep assistant 218 may use to determine adjustments to be made to the physical environment in response to the user's physiological activity.

At block 410, the system 100 selects a virtual environment to be presented by the virtual reality device 240. As noted earlier, there are many different types of virtual environments that can be presented; for example, aquatic scenes (e.g., aquarium or ocean), general nature scenes, or other environments that are designed to promote sleep. The system 100 can select a specific virtual environment in response to user input, as a result of default settings of the virtual sleep assistant 218, or by accessing user customization data 344 (such as a user profile or preferences). Once the virtual environment is selected, the system 100 presents an initial stage of the virtual environment until a sufficient amount of biofeedback information is received to allow the system 100 to begin making dynamic adjustments to the virtual environment.

At block 412, the system 100 receives physiological signals output by the physiological sensor(s) 232, 262, which represent physiological activity of a person using the system 100. At block 414, the system 100 processes the physiological signals received at block 412 and determines one or more physiological parameters and the current parameter values (e.g., breathing rate: 10 breaths per minute) as of the sampling instance. The parameter values can be calculated or estimated (e.g., based on a number of breaths detected in a given time interval). The parameter values can be determined by, for example, a computer-processing unit of the mobile or wearable computing device 210, or in computer processing units located directly in the physiological sensor(s) 232, 262. At block 416, the system 100 determines a stage of the immersive virtual environment to present, based on the current parameter values. In an illustrative embodiment, the process at block 416 includes a mapping function in a form of a look-up table that maps physiological parameter values to stages of the virtual environment. As shown in TABLE 1 below, each immersive virtual environment can be divided into a number of successive stages that can be presented to the user. Each stage relates to a physiological parameter value or a range of physiological parameter values. That is, where a physiological parameter has a range of possible values, each stage of the virtual environment relates to a different subset of the range of possible values. TABLE 1 illustrates the relationship between a few exemplary visual and audio features of an immersive virtual environment and an exemplary physiological parameter.

TABLE 1

Physiological Parameter Mapping - Respiration Rate

| | | | VISUAL FEATURES | | |
|---|---|---|---|---|---|
| STAGE | PHYSIOLOGICAL PARAMETER Respiration Rate (bpm) | AUDIO FEATURES Audio Gains | Number of Primary Foreground Elements | Speed of Object Movement | Densities of Secondary Foreground Elements |
| 4 | 6 | 0.9 | 13 | 0.08 | 0.04/0.03/0.03 |
| 3 | 8 | 0.2 | 08 | 1.2 | 0.02/0.02/0.02 |

TABLE 1-continued

Physiological Parameter Mapping - Respiration Rate

| STAGE | PHYSIOLOGICAL PARAMETER Respiration Rate (bpm) | AUDIO FEATURES Audio Gains | VISUAL FEATURES | | |
|---|---|---|---|---|---|
| | | | Number of Primary Foreground Elements | Speed of Object Movement | Densities of Secondary Foreground Elements |
| 2 | 12 | 0.03 | 05 | 1.7 | 0.02/0.01/0.01 |
| 1 | 16 | 0.003 | 01 | 2.3 | 0.01/0.007/0.006 |

In the example of TABLE 1, a single physiological parameter (respiration rate) is mapped to both visual and audio elements of an immersive virtual environment. Each value of the physiological parameter corresponds to a different stage of the immersive virtual environment, and each stage of the immersive virtual environment relates to audio and visual features that have different values. The illustrative audio feature is gain (e.g., volume) and the illustrative visual features are the number of primary foreground elements (e.g., fish in the example of FIG. 1), the speed of object movement (e.g., the speed at which the fish travel across the display), and the densities of secondary foreground elements (e.g., the density of the bubbles of FIG. 1). In general, low respiration rate promotes heart rate variability and, consequently, decreases heart rate. Heart rate variability has been found to significantly increase at a respiratory frequency of 6 breaths per minute. Inducing low levels of physiological activity (e.g. lowering heart rate voluntarily via paced breathing) across the sleep onset process helps the system 100 to reduce the elevated level of psychophysiological activity (which is typical in insomnia or other condition involving elevated stress and anxiety)) at the beginning of the sleep session and helps the individual fall asleep. In sleep research, 6 breaths per minute corresponds to a target breathing rate for obtaining maximum relaxation. Thus, in TABLE 1, the higher breathing rates correspond to earlier stages in the succession of virtual environment stages, and lower breathing rates correspond to later stages. According to the example of TABLE 1, the virtual environment becomes more immersive (presenting a higher number of primary foreground elements, a higher density of secondary foreground elements, and louder audio, as the respiration rate decreases. However, the speed of movement of the displayed objects becomes slower as the respiration rate decreases. Using a mapping such as illustrated by TABLE 1 enables the system 100 to gradually present a more immersive experience if the user increases his or her relaxation and reacts favorably to the previously-presented stage of the virtual environment. In the illustrated embodiments, the system 100 increases the degree of virtual immersion in response to reductions in the user's respiration rate. Once the user's respiration has decreased, the system 100 can make adjustments to the immersive virtual environment 116 based on other criteria, such as the previously-presented stages of the immersive virtual environment 116 (e.g., adjust the quantity or speed of visual features based on the quantity or speed of the visual features presented in the previous stage).

In TABLE 2 below, an illustrative example of a mapping function relating to the use of muscle activity as primary feedback parameter is shown. As discussed above, system 100 can adjust the immersive virtual environment 116 (and/or an aspect of user's physical environment) in response to the detection of the user's muscle activity. For example, two electromyogram (EMG) sensors can be incorporated in a "sleep mask" to detect the muscle activity of corrugator supercilii muscle (by detecting the electrical potential generated by muscle bundles). The resting EMG tone may be recorded for a short time (e.g. 1 min) when the user is lying down in bed maintaining their neutral "position," to determine the baseline EMG tone (µv). The individual may then be instructed or coached by the sleep assistant 218 to decrease his or her level of "muscle contraction" in his or her facial muscles, and particularly in the forehead (or, of course, the user may do so on his or her own, without coaching). The stages of immersion in the virtual environment 116 may increase based on the percentage decrease in muscle contraction from the baseline levels.

TABLE 2

Physiological Parameter Mapping - Muscle Activity.

| STAGE | PHYSIOLOGICAL PARAMETER Muscle Tone (% changes respect to baseline levels) | AUDIO FEATURES Audio Gains | VISUAL FEATURES | | |
|---|---|---|---|---|---|
| | | | Number of Primary Foreground Elements | Speed of Object Movement | Densities of Secondary Foreground Elements |
| 4 | −60 | 0.9 | 13 | 0.08 | 0.04/0.03/0.03 |
| 3 | −30 | 0.2 | 08 | 1.2 | 0.02/0.02/0.02 |
| 2 | −10 | 0.03 | 05 | 1.7 | 0.02/0.01/0.01 |
| 1 | Individuals' baseline levels (in µV) | 0.003 | 01 | 2.3 | 0.01/0.007/0.006 |

Of course, the mechanics of each stage of the immersive virtual environment are not limited to types of features and mappings shown in TABLE 1 and TABLE 2 or the data values shown in TABLE 1 and TABLE 2. Other strategies for dynamically changing the immersive virtual environment to induce sleep are within the scope of this disclosure.

At block 418, the immersive virtual environment is presented using the virtual reality device 240. To do this, the system 100 constructs the appropriate stage of the immersive virtual environment and transmits the stage content and control commands to the virtual reality device 240. Once received, the virtual reality device 240 executes the commands to presenting the virtual environment. In some embodiments, portions of the stage content (e.g., the visual elements and/or audio elements) may be stored in the virtual reality device 240, such that the system 100 only transmits control commands to the device 240.

To accomplish dynamic changes in the virtual environment, the system 100 processes frequent physiological feedback data from the sensors 232, 262. For example, the system 100 may process the physiological data at a frequency that corresponds to the internal sampling rate of the computing device 210 (e.g., 100 Hz for a standard smart phone). At block 420, the system 100 receives new physiological signals that are detected subsequent to the presentation of the stage of the virtual environment at block 418. At block 422, new physiological parameter values are calculated from the new physiological signals received at block 420.

The system 100 considers whether to continue the biofeedback virtual reality sleep promotion at block 424. If it is determined that the virtual reality sleep promotion is to be discontinued, then the method 400 concludes at block 428 and the system 100 discontinues the presentation of the virtual environment. In some embodiments, the virtual reality sleep promotion is discontinued by a timer set to turn the sleep assistant 218 off after sleep promotion has been running for a certain period of time. In other embodiments, the virtual reality sleep promotion may be stopped due to an input from a user. In still other embodiments, the system 100 determines a sleep state based on the physiological signals or using a gaze detector incorporated into the virtual sleep assistant hardware that detects the user closing his or her eyes. In some cases, the system 100 may turn off the virtual sleep assistant 218 upon detecting the closing of the person's eyes, or turn off only the visual display when the eyes of the user are closed.

In yet another embodiment, the physiological feedback data may be used to detect a state of full sleep, or a state sufficiently close to full sleep, and turn off the sleep assistant 218 after certain physiological conditions have been met. As an example, the system 100 can detect, based on the physiological signals, whether a person has fallen asleep or wishes to discontinue using the system 100 as follows. When the person begins using the system 100, they begin by consciously slowing their breathing rate, and the system 100 detects a low breathing rate. However, when people fall asleep, they lose the voluntary control of their own breathing. Therefore, once the person falls asleep, their breathing rate returns to "normal," and the system 100 detects an increase in the breathing rate relative to the previously-slowed breathing rate (e.g., the breathing rate voluntarily slowed by the user performing a relaxation technique while conscious). The system 100 can thus turn off the sleep assistant application 218 when the system 100 detects a normal breathing rate for a certain period of time (e.g. when the person falls asleep) after having previously detected a low breathing rate for a certain period of time. A return to a normal breathing rate could also mean that the user has discontinued the voluntary slow breathing the person does not want use the device anymore. In this case as well, the system 100 can turn off the sleep assistant application 218 in response to the return to a normal breathing rate. In this way, the sleep assistant 218 is configured to guide individuals toward sleep, starting from a conscious level (which typically occurs at the beginning of the night, when the person is still awake), through intermediate stages in which users use the VR biofeedback system, up to the point at which when they fall sleep (unconsciousness). During the intermediate stages, the system 100 automatically adjusts the immersive virtual environment (by increasing the sense of presence or degree of immersiveness) so that the user progressively feels that the (unreal) virtual environment is actually their real (physical) environment. As the user's sense of presence in the virtual environment increases, the user's mind is distracted from aspects of their real environment that normally disrupt sleep (such as physical features of the room, emotional connections with the physical environment, and thoughts of worry and rumination).

If the virtual reality sleep promotion is to be continued, the system 100 determines whether the stage of the virtual environment (and/or an aspect of the physical environment, e.g., a setting of a smart device 266) is to be changed, at block 426. The determination as to whether to change the virtual and/or physical environment can be made in the same manner as described in block 416. That is, the system maps the new physiological parameter values determined at block 422 to a stage of the virtual and/or physical environment (using, e.g., one or more mapping functions 234). The new parameter values may relate to the stage(s) of the virtual and/or physical environments that are currently being presented, in which no change is made to the virtual and/or physical environment, and the system 100 returns to block 418 and continues presenting the same stage of the virtual and/or physical environment(s) as was done previously. If the new parameter values relate to a different stage of the virtual and/or physical environment(s) than the stage that is currently being presented, the system 100 returns to block 416 and proceeds to determine the specifications for and present the new stage. In other embodiments, the decision at block 426 may be performed by comparing the old physiological parameter value determined at block 414 to the new physiological parameter determined at block 422. If the old physiological parameter value and the new physiological parameter value are the same or within an acceptable range of difference, the system 100 continues presenting the current stage of the virtual and/or physical environment(s), and the process of monitoring physiological signals continues. If the old physiological parameter value and the new physiological parameter value are different or outside an acceptable range of difference, then the stage of the virtual and/or physical environment(s) is updated to correspond to the new physiological parameters, and the process of monitoring physiological signals continues.

Figure 5:
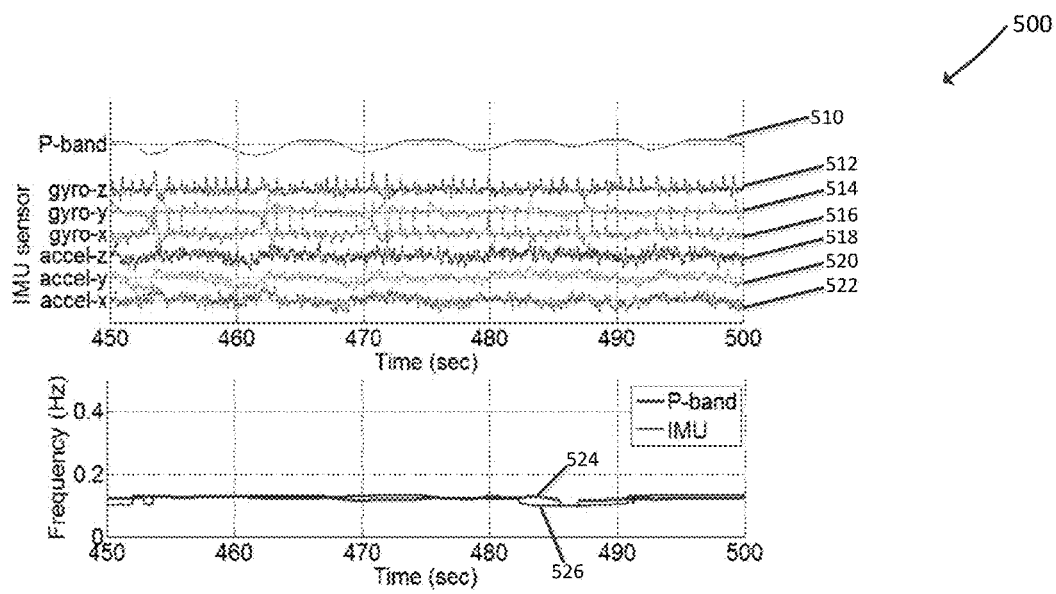
FIG. 5 is a simplified plot illustrating diaphragmatic breathing at approximately 6 breaths per minute during use of at least one embodiment of the sleep assistant of FIG. 1 prior to the onset of sleep. In the figure, breathing data recorded by the Piezoelectric bands and IMU sensor are overlapped to illustrate the reliability of the computing device (e.g., a smart phone) in detecting breathing rate under slow breathing conditions.
Figure 6:
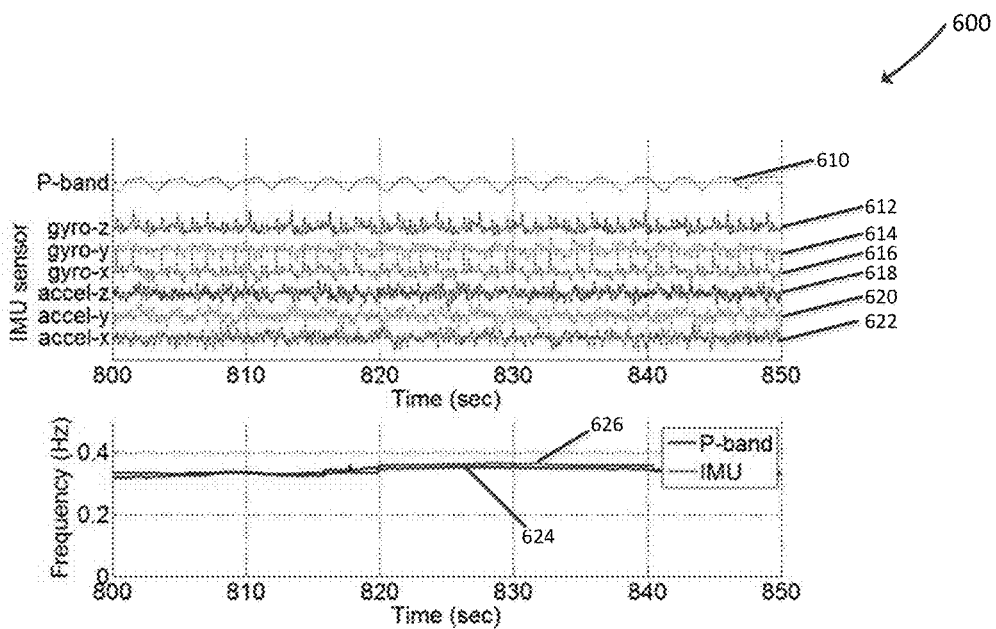
FIG. 6 is a simplified plot illustrating normal breathing frequency during a period of sleep, immediately following the sleep onset. In the figure, breathing data recorded by the Piezoelectric bands and IMU sensor are overlapped to illustrate the reliability of the computing device (e.g., a smart phone) in detecting breathing rate under normal breathing conditions.

Referring now to FIGS. 5 and 6, illustrative plots of sensor data are shown, which compare the use of an inertial measurement unit (IMU) to measure respiration rate to the results obtained using a piezo respiratory effort band ("p-band"), which is the conventional "gold standard" method used to capture respiration data during polysomnographic sleep recordings. In FIG. 5, the plot 500 shows low frequency breathing of a person during controlled feedback relaxation induced by the sleep assistant 218, but prior to sleep. Graph line 510 shows the breathing frequency measured by the p-band over time. Graph lines 512, 514, 516, 518, 520, and 522 show the six outputs of an IMU measuring the respiration rate over time. Typically, an IMU comprises a three-axis accelerometer and a three-axis gyroscope. Breathing frequency is estimated by analyzing accelerometer data and combining it with gyroscope data, if available. A smoothing function (such as that which may be provided by a smart phone application) may be used to delay the feedback response and thereby compensate for breathing changes that result from the user's body movements or other artifacts.

Graph line 524 shows the breathing frequency (in Hertz) of a person as measured by the p-band, and graph line 526 shows the breathing frequency of a person measured using the IMU. Both the p-band and the IMU measurement techniques exhibit similar performance. The plot 600, found in FIG. 6, is nearly identical to the graph 500, found in FIG. 5, except that the plot 600 is a measurement of breathing frequency of a person during a period of sleep. Graph lines 610 and 624 relate to the p-band measurements, and graph lines 612, 614, 616, 618, 620, 622, and 626 relate to the IMU measurements. Again, the p-band and the IMU exhibit similar performance.

It should be noted that the breathing rate can be affected by artifacts such as body movements, which usually occur at the sleep onset (e.g., people turning over or changing position, etc.) In some embodiments, in order to avoid rapid changes in the feedback output due to body movements, the system 100 executes a function (e.g., a smoothing function) to correct the artifact before providing the feedback to the sleep assistant 218.

Referring now to FIGS. 7-9, exemplary plots of test results obtained during trials illustrate the effectiveness of an embodiment of the sleep assistant 218 in comparison to a baseline night in which the sleep assistant 218 was not used. FIG. 7 shows that a lower heart rate is established during an initial period of low breathing rate using the sleep assistant 218 and the lower heart rate is maintained after the onset of sleep. FIG. 8 shows that in the same trial, the lower heart rate was established with the sleep assistant 218 prior to sleep and maintained during both rapid eye movement (REM) and non-rapid eye movement (NREM) periods of sleep, across the whole night. FIG. 9 compares a measure of sleep quality for a baseline night in which the sleep assistant 218 was not used and a night in which the sleep assistant 218 was used, and shows that sleep quality improved with the use of the sleep assistant 218.

Additional Examples

Illustrative examples of the technologies disclosed herein are provided below. An embodiment of the technologies may include any one or more, and any combination of, the examples described below.

In an example 1, a method for promoting sleep includes, with a biofeedback virtual reality system: monitoring a physiological signal received from a sensor over time; presenting an immersive virtual environment with a virtual reality device, the immersive virtual environment comprising a display of visual elements designed to promote sleep; detecting a change in the physiological signal, and in response to the detected change in the physiological signal: applying biofeedback technology to determine an adjustment to the immersive virtual environment, wherein the adjustment is to change the display of visual elements; and presenting the adjustment to the immersive virtual environment with the virtual reality device.

In an example 2, the method includes the subject matter of example 1 and includes receiving the physiological signal at a mobile or wearable sensing and computing device, and determining one or more physiological parameters based on the physiological signal. In an example 3, the method includes the subject matter of example 1 or example 2 and includes presenting the immersive virtual environment is in response to a user actively attempting to control a physiological parameter being sensed by the sensor. In an example 4, the method includes the subject matter of any of the preceding examples and includes selecting the immersive virtual environment from a plurality of stored immersive virtual environments based on the physiological signals and/or user customization data. In an example 5, the method includes the subject matter of any of the preceding examples and includes determining user customization data and determining the adjustment to the immersive virtual environment based on the user customization data. In an example 6, the method includes the subject matter of any of the preceding examples and includes, wherein the immersive virtual environment comprises an audio soundtrack, applying biofeedback technology to determine an adjustment to the audio soundtrack and applying the adjustment to the audio soundtrack with the virtual reality device. In an example 7, the method includes the subject matter of any of the preceding examples and includes determining a mapping defining a relationship between physiological signals and elements of the immersive virtual environment, wherein the mapping is defined to promote sleep, and using the mapping to determine the adjustment to the immersive virtual environment. In an example 8, the method includes the subject matter of any of the preceding examples and includes storing data relating to adjustments made to the immersive virtual environment over time and physiological signals monitored after the adjustments have been made, applying an artificial intelligence or machine learning technique to the stored data to algorithmically learn a modification to the mapping; and updating the mapping to include the learned modification.

In an example 9, the method includes the subject matter of any of the preceding examples and includes detecting a sleep state based on the monitoring of the physiological signal and turning off the display of visual elements in response to the sleep state. In an example 10, the method includes the subject matter of any of the preceding examples and includes, wherein the physiological signal represents a respiration rate or a heart rate or muscle activity, the monitoring detects a change in the respiration rate, heart rate, or muscle activity, in response to the change in the respiration rate, heart rate or muscle activity, changing a speed, quantity, density, frequency, color, brightness, contrast, direction, depth, focus, point of view, and/or complexity of one or more of the visual elements in the presentation of the immersive virtual environment. In an example 11, the method includes the subject matter of any of the preceding examples and includes, wherein the immersive virtual environment further comprises an audio soundtrack, changing the volume, content, speed, complexity, and/or intensity of the audio soundtrack in response to the change in the respiration rate or heart rate. In an example 12, the method includes the subject matter of any of the preceding examples and includes, wherein the physiological signal represents a respiration rate or a heart rate, the monitoring detects a decrease in the respiration rate or heart rate, and the method comprises, in response to the decrease in the respiration rate or heart rate, decreasing speed, and increasing quantity, density and/or frequency of one or more of the visual elements in the presentation of the immersive virtual environment. In an example 13, the method includes the subject matter of any of the preceding examples and includes, wherein the immersive virtual environment further comprises an audio soundtrack, increasing the volume or degree of surround sound at which the audio soundtrack is played in response to the decrease in the respiration rate or heart rate. In an example 14, the method includes the subject matter of any of the preceding examples and includes, wherein the physiological signal represents a respiration rate or a heart rate or a rate of muscle activity, the monitoring detects an increase in the respiration rate or heart rate or muscle activity, in response to the increase in the respiration rate or heart rate or muscle activity, increasing speed, and decreasing quantity, density, and/or frequency of one or more of the visual elements in the presentation of the immersive virtual environment.

In an example 15, the method includes the subject matter of any of the preceding examples and includes decreasing the volume at which the audio soundtrack is played in response to the increase in the respiration rate or heart rate. In an example 16, the method includes the subject matter of any of the preceding examples and includes determining a value of a physiological parameter based on the physiological signal, wherein the physiological parameter has a range of possible values, the immersive virtual environment comprises a plurality of visual stages, each of the visual stages comprises a different arrangement of visual elements, each of the visual stages corresponds to a different subset of the range of possible values of the physiological parameter, determining the adjustment comprises selecting a visual stage corresponding to the determined value of the physiological parameter, and presenting the adjustment comprises presenting the selected visual stage. In an example 17, the method includes the subject matter of any of the preceding examples and includes, wherein the immersive virtual environment comprises a plurality of audio stages, each of the audio stages comprises a different arrangement of audio elements, each of the audio stages corresponds to a different subset of the range of possible values of the physiological parameter, determining the adjustment comprises selecting an audio stage corresponding to the determined value of the physiological parameter, and presenting the adjustment comprises presenting the selected audio stage. In an example 18, the method includes the subject matter of any of the preceding examples and includes determining, a value of a physiological parameter from the physiological signal, wherein the physiological parameter comprises a respiration rate, a heart rate, an electroencephalography (EEG) measurement, a measure of muscle activity, and/or a human body temperature, and determining the adjustment to the immersive virtual environment based on the value of the physiological parameter. In an example 19, the method includes the subject matter of any of the preceding examples and includes, wherein the immersive virtual environment further comprises an audio soundtrack, determining a visual adjustment to adjust the display of visual elements and determining an audio adjustment to adjust the audio soundtrack. In an example 20, the method includes the subject matter of any of the preceding examples and includes determining the visual adjustment independently of the determining of the audio adjustment. In an example 21, the method includes the subject matter of any of the preceding examples and includes, wherein the immersive virtual environment comprises a plurality of different sensory stimuli, independently adjusting each of the different sensory stimuli in response to the change in the physiological signal.

An example 22 includes a biofeedback virtual reality system for promoting sleep, the biofeedback virtual reality system including: a sensor to detect a physiological signal; a mobile or wearable computing device to: receive the physiological signal; determine a value of a physiological parameter based on the physiological signal; map the value of the physiological parameter to a stage of an immersive virtual environment of a plurality of stored immersive virtual environments, each of the stored immersive virtual environments comprising a succession of stages designed to promote sleep, each of the stages comprising a different arrangement of sensory stimuli; and a virtual reality device in communication with the mobile or wearable computing device, the virtual reality device to present the stage of the immersive virtual environment; wherein the mobile or wearable computing device is to determine a new value of the physiological parameter and map the new value of the physiological parameter to a new stage of the immersive virtual environment; and wherein the virtual reality device is to present the new stage of the immersive virtual environment in response to the new value of the physiological parameter.

In an example 23, the system includes the subject matter of example 22, wherein the mobile or wearable computing device comprises a smartphone, a tablet computer, an attachable/detachable device, a smart watch, smart glasses, a smart wristband, smart jewelry, and/or smart apparel. In an example 24, the system includes the subject matter of example 22 or example 23, wherein at least two of the mobile or wearable computing device, the virtual reality device, and the sensor are embodied as a unitary device. In an example 25, the system includes the subject matter of any of examples 22-24, wherein the mobile or wearable computing device receives the physiological signal through wireless communication and/or the mobile or wearable computing device communicates with the virtual reality device through wireless communication. In an example 26, the system includes the subject matter of any of examples 22-25, wherein the sensor comprises a motion sensor, and wherein the mobile or wearable computing device determines a respiration rate from the output of the motion sensor. In an example 27, the system includes the subject matter of any of examples 22-26, wherein the mobile or wearable computing device comprises a positioner to position the mobile or wearable computing device to detect human body motion indicating breathing. In an example 28, the system includes the subject matter of any of examples 22-27, wherein the mobile or wearable computing device is to receive a plurality of different physiological signals, determine a value of each of a plurality of different physiological parameters based on the plurality of different physiological signals, and determine a stage of the immersive virtual environment based on the values of the different physiological parameters. In an example 29, the system includes the subject matter of any of examples 22-28, wherein the immersive virtual environment comprises an arrangement of visual elements including an avatar that interacts with the immersive virtual environment in response to the physiological signal. In an example 30, the system includes the subject matter of any of examples 22-29, comprising a gaze detector in communication with the mobile or wearable computing device, wherein the mobile or wearable computing device is to manipulate the immersive virtual environment in response to output of the gaze detector. In an example 31, the system includes the subject matter of any of examples 22-30, wherein the virtual reality device comprises virtual reality eyewear and headphones. In an example 32, the system includes the subject matter of any of examples 22-31, wherein the virtual reality device comprises high-definition video glasses, a non-rigid sleep mask, a television, a projector to project a display of visual elements onto a wall or ceiling, and/or one or more remote speakers.

An example 33 includes a biofeedback virtual reality sleep assistant embodied in one or more computer accessible media, the biofeedback virtual reality sleep assistant including: a physiological signal processor to receive one or more physiological signals from one or more sensing devices; a physiological signal processing module to monitor one or more physiological parameters from the one or more physiological signals over time, each of the physiological parameters having a range of possible values, and to determine a value of each of the physiological parameters at a plurality of different instances in time; a physiological parameter mapping module to map the values of the one or more physiological parameters at an instance in time to a stage of an immersive virtual environment selected from a plurality of stored immersive virtual environments, each of the immersive virtual environments comprising at least a visual display and an audio soundtrack, each of the visual display and the audio soundtrack having a plurality of successive stages designed to promote sleep; and an immersive environment control module to present the stage of the selected immersive virtual environment by one or more virtual reality devices; wherein the physiological signal processing module is to detect changes in the values of the one or more physiological parameters over time; and wherein the physiological parameter mapping module is to change the stage of the selected immersive virtual environment in response to the changes in the values of the one or more physiological parameters.

In an example 34, the sleep assistant includes the subject matter of claim 33, wherein the physiological parameter mapping module map the values of the one or more physiological parameters to a stage of an immersive virtual environment by executing a continuous mapping function or by accessing a lookup table. In an example 35, the sleep assistant includes the subject matter of claim 33, wherein the physiological parameter mapping module is to map the values of the one or more physiological parameters to a stage of the visual display and separately map the values of the one or more physiological parameters to a stage of the audio soundtrack. In an example 36, the sleep assistant includes the subject matter of claim 33, wherein the immersive environment control module is to construct the selected immersive virtual environment in real time by adding, deleting, or changing elements of the visual display and/or the audio soundtrack based on the values of the one or more physiological parameters. In an example 37, the sleep assistant includes the subject matter of claim 33, wherein the immersive environment control module is to communicate with a smart device to control an aspect of a physical environment in response to changes in the values of the one or more physiological parameters over time.

An example 38 includes an article of manufacture including, embodied in one or more computer accessible storage media: an immersive virtual environment comprising a display of visual elements and an audio soundtrack, wherein the display and the audio soundtrack each have a plurality of stages that are coordinated with different values of at least one physiological parameter.

General Considerations

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to effect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine (e.g., a computing device or a "virtual machine" running on one or more computing devices). For example, a machine-readable medium may include any suitable form of volatile or non-volatile memory.

Modules, data structures, and the like defined herein are defined as such for ease of discussion, and are not intended to imply that any specific implementation details are required. For example, any of the described modules and/or data structures may be combined or divided into sub-modules, sub-processes or other units of computer code or data as may be required by a particular design or implementation.

In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application-programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure.

This disclosure is to be considered as exemplary and not restrictive in character, and all changes and modifications that come within the spirit of the disclosure are desired to be protected.

The invention claimed is:

1. A computer-implemented method, comprising:
receiving, at a computing device, a physiological signal;
determining, at a first point in time, a first physiological state, wherein the first physiological state is determined using the physiological signal;
using the first state to determine a virtual reality environment, wherein the virtual reality environment includes a computer-generated visual display;
enabling the virtual reality environment;
monitoring the physiological signal;
detecting, at a second point in time, whether a change in the physiological signal has occurred;
determining an adjustment to the virtual reality environment, wherein a detected change in the physiological signal is used to determine the adjustment, and wherein the determined adjustment is configured to induce a second state; and adjusting the virtual reality environment using the determined adjustment, wherein adjusting the virtual reality environment includes modifying the visual display to induce the second state.

2. The computer-implemented method of claim 1, wherein the visual display includes one or more graphical elements, wherein the one or more graphical elements are rendered in real time.

3. The computer-implemented method of claim 2, wherein, at a point in time, a rendering of the one or more graphical elements uses a value for the physiological signal detected at a previous point in time.

4. The computer-implemented method of claim 1, wherein the physiological signal includes motion detection, and wherein the visual display is configured to react in real time to changes in the motion detection.

5. The computer-implemented method of claim 1, wherein the physiological signal includes gaze detection, and wherein the visual display is configured to react in real time to changes in the gaze detection.

6. The computer-implemented method of claim 1, wherein the virtual reality environment further includes an audio signal, and wherein the adjusting the virtual reality environment further includes adjusting the audio signal to induce the second state.

7. The computer-implemented method of claim 6, wherein the audio signal is coordinated with the visual display.

8. The computer-implemented method of claim 1, wherein the virtual reality environment includes control signals for controlling environmental devices in a physical location, and wherein the enabling the virtual reality environment includes transmitting the control signals.

9. The computer-implemented method of claim 8, wherein the adjusting the virtual reality environment further includes adjusting the control signals.

10. The computer-implemented method of claim 1, further comprising:
determining an association between the physiological signal and parameters for the virtual reality environment; and
using the determined association to modify stored parameters for the virtual reality environment.

11. The computer-implemented method of claim 1, wherein the virtual reality environment includes one or more stages, and wherein a stage includes an arrangement of sensory stimuli.

12. The computer-implemented method of claim 11, further comprising:
determining, at the first point in time, a first value for the physiological signal; and
using the first value to select a first stage from the one or more stages.

13. The computer-implemented method of claim 11, further comprising:
determining, at the second point in time, a second value for the physiological signal;
using the second value to select a second stage from the one or more stages; and
using the second stage to determine the adjustment to the virtual reality environment.

14. The computer-implemented method of claim 11, where stimuli in the arrangement of sensory stimuli are individually adjustable.

15. The computer-implemented method of claim 1, further comprising:

determining, at a third point in time, a current value for the physiological signal;
using the current value to determine whether the second state has been induced;
determining an additional adjustment to the virtual reality environment, wherein the additional adjustment is configured to induce a third state; and
adjusting the virtual reality environment using the additional adjustments.

16. The computer-implemented method of claim 1, further comprising
determining, at a third point in time, a current value for the physiological signal;
using the current value to determine that the second state has been induced; and
disabling the virtual reality environment.

17. A computing device, comprising:
one or more processors; and
a non-transitory computer-readable medium including instructions that, when executed by the one or more processors, cause the one or more processors to perform operations including:
receiving, at the computing device, a physiological signal;
determining, at a first point in time, a first physiological state, wherein the first physiological state is determined using the physiological signal;
using the first physiological state to determine a virtual reality environment, wherein the virtual reality environment includes a computer-generated visual display;
enabling the virtual reality environment;
monitoring the physiological signal;
detecting whether, at a second point in time, the physiological signal has changed;
determining an adjustment to the virtual reality environment, wherein a detected change in the physiological signal is used to determine the adjustment, and wherein the determined adjustment is configured to induce a second state; and
adjusting the virtual reality environment, wherein adjusting the virtual reality environment includes modifying the interactive computer-generated visual display to induce the second physiological state.

18. The computing device of claim 17, wherein the interactive computer-generated visual display includes one or more graphical elements, wherein the one or more graphical elements are rendered in real time.

19. The computing device of claim 18, wherein, at a point in time, a rendering of the one or more graphical elements uses a value for the physiological signal detected at a previous point in time.

20. The computing device of claim 17, wherein the physiological signal includes motion detection, and wherein the interactive computer-generated visual display is configured to react in real time to changes in the motion detection.

21. The computing device of claim 17, wherein the physiological signal includes gaze detection, and wherein the interactive computer-generated visual display is configured to react in real time to changes in the gaze detection.

22. The computing device of claim 17, wherein the virtual reality environment further includes an audio signal, and wherein the adjusting the virtual reality environment further includes adjusting the audio signal to induce the second state.

23. The computing device of claim 22, wherein the audio signal is coordinated with the interactive computer-generated visual display.

24. The computing device of claim 17, wherein the virtual reality environment includes control signals for controlling environmental devices in the existing physical environment, and wherein the enabling the virtual reality environment includes transmitting the control signals.

25. The computing device of claim 24, wherein the adjusting the virtual reality environment further includes adjusting the control signals.

26. The computing device of claim 17, wherein the non-transitory computer-readable medium further includes instructions that, when executed by the one or more processors, cause the one or more processors to perform operations including:
determining an association between the physiological signal detected at the point in time and parameters for the virtual reality environment; and
using the determined association to modify stored parameters for the virtual reality environment.

27. The computing device of claim 17, wherein the virtual reality environment includes one or more stages, and wherein a stage includes an arrangement of sensory stimuli.

28. The computing device of claim 27, wherein the non-transitory computer-readable medium further includes instructions that, when executed by the one or more processors, cause the one or more processors to perform operations including:
determining, at the first point in time, a first value for the physiological signal; and
using the first value to select a first stage from the one or more stages.

29. The computing device of claim 27, wherein the non-transitory computer-readable medium further includes instructions that, when executed by the one or more processors, cause the one or more processors to perform operations including:
determining, at the second point in time, a second value for the physiological signal;
using the second value to select a second stage from the one or more stages; and
using the second stage to determine the adjustment to the virtual reality environment.

30. The computing device of claim 27, where one or more stimuli in the arrangement of sensory stimuli are individually adjustable.

31. The computing device of claim 17, wherein the non-transitory computer-readable medium further includes instructions that, when executed by the one or more processors, cause the one or more processors to perform operations including:
determining, at a third point in time, a current value for the physiological signal;
using the current value to determine whether the second state has been induced;
determining an additional adjustment to the virtual reality environment, wherein the additional adjustment is configured to induce a third state; and
adjusting the virtual reality environment using the additional adjustments.

32. The computing device of claim 17, wherein the non-transitory computer-readable medium further includes instructions that, when executed by the one or more processors, cause the one or more processors to perform operations including:
determining, at a third point in time, a current value for the physiological signal;
using the current value to determine whether the second state has been induced; and
disabling the virtual reality environment.

33. A computer-program product tangibly embodied in a non-transitory machine-readable storage medium, including instructions that, when executed by one or more processors, cause the one or more processors to:
receive, at a computing device, a physiological signal;
determine, at a first point in time, a first physiological state, wherein the first physiological state is determined using the physiological signal;
use the first physiological state to determine a virtual reality environment, wherein the virtual reality environment includes a computer-generated visual display;
enable the virtual reality environment; monitor the physiological signal;
detect, at a second point in time, a change in the physiological signal;
determine an adjustment to the virtual reality environment, wherein the detected change in the physiological signal is used to determine the adjustment, and wherein the determined adjustment is configured to induce a second state; and
adjust the virtual reality environment, wherein adjusting the virtual reality environment includes modifying the interactive computer-generated visual display to induce the second physiological state.

34. The computer-program product of claim 33, wherein the interactive computer-generated visual display includes one or more graphical elements, wherein the one or more graphical elements are rendered in real time.

35. The computer-program product of claim 34, wherein, at a point in time, a rendering of the one or more graphical elements uses a value for the physiological signal detected at a previous point in time.

36. The computer-program product of claim 33, wherein the physiological signal includes motion detection, and wherein the interactive computer-generated visual display is configured to react in real time to changes in the motion detection.

37. The computer-program product of claim 33, wherein the physiological signal includes gaze detection, and wherein the interactive computer-generated visual display is configured to react in real time to changes in the gaze detection.

38. The computer-program product of claim 33, wherein the virtual reality environment further includes an audio signal, and wherein adjusting the virtual reality environment further includes adjusting the audio signal to induce the second state.

39. The computer-program product of claim 38, wherein the audio signal is coordinated with the interactive computer-generated visual display.

40. The computer-program product of claim 33, wherein the virtual reality environment includes control signals for controlling environmental devices in the existing physical environment, and wherein enabling the virtual reality environment includes transmitting the control signals.

41. The computer-program product of claim 40, wherein adjusting the virtual reality environment further includes adjusting the control signals.

42. The computer-program product of claim 33, further comprising instructions that, when executed by the one or more processors, cause the one or more processors to:
determine an association between the physiological signal and parameters for the virtual reality environment; and
use the determined association to modify stored parameters for the virtual reality environment.

43. The computer-program product of claim 33, wherein the virtual reality environment includes one or more stages, and wherein a stage includes an arrangement of sensory stimuli.

44. The computer-program product of claim 43, further comprising instructions that, when executed by the one or more processors, cause the one or more processors to:
  determine, at the first point in time, a first value for the physiological signal; and
  use the first value to select a first stage from the one or more stages.

45. The computer-program product of claim 43, further comprising instructions that, when executed by the one or more processors, cause the one or more processors to:
  determine, at the second point in time, a second value for the physiological signal;
  use the second value to select a second stage from the one or more stages; and
  use the second stage to determine the adjustment to the virtual reality environment.

46. The computer-program product of claim 43, where one or more stimuli in the arrangement of sensory stimuli are individually adjustable.

47. The computer-program product of claim 33, further comprising instructions that, when executed by the one or more processors, cause the one or more processors to:
  determine, at a third point in time, a current value for the physiological signal;
  use the current value to determine whether the second state has been induced;
  determine an additional adjustment to the virtual reality environment, wherein the additional adjustment is configured to induce a third state; and
  adjust the virtual reality environment using the additional adjustments.

48. The computer-program product of claim 33, further comprising instructions that, when executed by the one or more processors, cause the one or more processors to:
  determine, at a third point in time, a current value for the physiological signal;
  use the current value to determine whether the second state has been induced; and
  disable the virtual reality environment.

* * * * *